(12) United States Patent
Forrest et al.

(10) Patent No.: US 11,149,255 B2
(45) Date of Patent: Oct. 19, 2021

(54) COMPOSITIONS AND METHODS FOR GENERATING REVERSION FREE ATTENUATED AND/OR REPLICATION INCOMPETENT VACCINE VECTORS

(71) Applicants: BioVentures, LLC, Little Rock, AR (US); The Research Foundation for the State University of New York, Albany, NY (US)

(72) Inventors: James Forrest, Little Rock, AR (US); Gang Li, Little Rock, AR (US); Laurie Krug, Albany, NY (US); Steven Skiena, Albany, NY (US)

(73) Assignees: BioVentures, LLC, Little Rock, AR (US); The Research Foundation for the State of University of New York, Albany, NY (US)

( * ) Notice: Subject to any disclaimer, the term of this patent is extended or adjusted under 35 U.S.C. 154(b) by 0 days.

(21) Appl. No.: 16/330,968

(22) PCT Filed: Sep. 6, 2017

(86) PCT No.: PCT/US2017/050229
§ 371 (c)(1),
(2) Date: Mar. 6, 2019

(87) PCT Pub. No.: WO2018/048869
PCT Pub. Date: Mar. 15, 2018

(65) Prior Publication Data
US 2019/0211313 A1    Jul. 11, 2019

Related U.S. Application Data

(60) Provisional application No. 62/383,907, filed on Sep. 6, 2016.

(51) Int. Cl.

| | |
|---|---|
| *C12N 7/00* | (2006.01) |
| *C12N 7/04* | (2006.01) |
| *C12N 15/86* | (2006.01) |
| *A61P 31/22* | (2006.01) |
| *A61K 39/12* | (2006.01) |
| *A61K 39/245* | (2006.01) |
| *A61K 39/00* | (2006.01) |

(52) U.S. Cl.
CPC ............... *C12N 7/00* (2013.01); *A61K 39/12* (2013.01); *A61K 39/245* (2013.01); *A61P 31/22* (2018.01); *C12N 7/04* (2013.01); *C12N 15/86* (2013.01); *A61K 2039/5254* (2013.01); *C12N 2710/16034* (2013.01); *C12N 2710/16043* (2013.01); *C12N 2710/16062* (2013.01); *C12N 2710/16434* (2013.01); *C12N 2710/16443* (2013.01); *C12N 2710/16452* (2013.01); *C12N 2740/10043* (2013.01)

(58) Field of Classification Search
CPC . C12N 7/00; C12N 7/04; C12N 15/86; C12N 2710/16043; C12N 2710/16443; C12N 2710/16434; C12N 2710/16452; C12N 2740/10043; C12N 2710/16034; C12N 2710/16062; A61P 31/22; A61K 39/12; A61K 39/245; A61K 2039/5254
See application file for complete search history.

(56) References Cited

U.S. PATENT DOCUMENTS

| | | | |
|---|---|---|---|
| 6,379,967 B1 * | 4/2002 | Meredith ............... | C12N 15/86 |
| | | | 435/456 |
| 9,273,288 B2 * | 3/2016 | Mason .................... | A61K 39/12 |
| 2010/0209454 A1 | 8/2010 | Wimmer et al. | |

FOREIGN PATENT DOCUMENTS

| | | |
|---|---|---|
| WO | 2000018906 A2 | 4/2000 |
| WO | 2000056365 A1 | 9/2000 |
| WO | 2003009869 A1 | 2/2003 |
| WO | 2018048869 A1 | 3/2018 |

OTHER PUBLICATIONS

Moser JM, Farrell ML, Krug LT, Upton JW, Speck SH. A gammaherpesvirus 68 gene 50 null mutant establishes long-term latency in the lung but fails to vaccinate against a wild-type virus challenge. J Virol. Feb. 2006;80(3):1592-8.*
Chattopadhyay A, Rose JK. Complementing defective viruses that express separate paramyxovirus glycoproteins provide a new vaccine vector approach. J Virol. Mar. 2011;85(5):2004-11. Epub Dec. 22, 2010.*
Lauring AS, Jones JO, Andino R. Rationalizing the development of live attenuated virus vaccines. Nat Biotechnol. Jun. 2010;28(6):573-9. Epub Jun. 7, 2010.*
Howe JA, Pelka P, Antelman D, Wilson C, Cornell D, Hancock W, et. al. Matching complementing functions of transformed cells with stable expression of selected viral genes for production of E1-deleted adenovirus vectors. Feb. 5, 2006;345(1):220-30. Epub Oct. 24, 2005. (Year: 2005).*
Zevenhoven-Dobbe JO, Greve S, van Tol H, Spaan WJM, Snijder EJ. Rescue of disabled infectious single-cycle (DISC) equine arteritis virus by using complementing cell lines that express minor structural glycoproteins. J Gen Virol. Dec. 2004;85(Pt 12):3709-3714. (Year: 2004).*

(Continued)

*Primary Examiner* — Rachel B Gill
(74) *Attorney, Agent, or Firm* — Polsinelli PC

(57) ABSTRACT

Provided herein are methods for generating reversion free attenuated and/or replication incompetent vaccine vectors and their use in vaccine compositions and vaccination. In particular, the use of a codon shuffled helper gene is used to produce compositions comprising replication incompetent virus.

20 Claims, 21 Drawing Sheets
(16 of 21 Drawing Sheet(s) Filed in Color)
Specification includes a Sequence Listing.

(56) References Cited

OTHER PUBLICATIONS

Barrett JW, Sun Y, Nazarian SH, Belsito TA, Brunetti CR, McFadden G. Optimization of codon usage of poxvirus genes allows for improved transient expression in mammalian cells. Virus Genes. Aug. 2006;33(1):15-26. (Year: 2006).*
Speck PG, Efstathiou S, Minson AC. In vivo complementation studies of a glycoprotein H-deleted herpes simplex virus-based vector. J Gen Virol. Oct. 1996;77 ( Pt 10):2563-8. (Year: 1996).*
Kovesdi I, Hedley SJ. Adenoviral producer cells. Viruses. Aug. 2010;2(8):1681-703. doi: 10.3390/v2081681. Epub Aug. 16, 2010. PMID: 21994701; PMCID: PMC3185730. (Year: 2010).*
Adler, H. et al., "Cloning and Mutagenesis of the Murine Gammaherpesvirus 68 Genome as an Infectious Bacterial Artificial Chromosome," J. Virol., Aug. 2000, pp. 6964-6974, vol. 74, No. 15.
Allen, R. et al., "Identification of an Rta responsive promoter involved in driving gammaHV68 v-cyclin expression during virus replication," Virology, 2007, pp. 250-259, vol. 365.
Almeida, A. et al., "Nasal Delivery of Vaccines," J. Drug Targeting, 1996, pp. 455-467, vol. 3, No. 6, Harwood Academic Publishers, GmbH, The Netherlands.
Barton, E. et al., "Pathogenesis and Host Control of Gammaherpesviruses: Lessons from the Mouse," Annu. Rev. Immunol., 2011, pp. 351-397, vol. 29.
Bergquist, C. et al., "Antibody responses in serum and lung to intranasal immunization with Haemophilus influenzae type b polysaccharide conjugated to cholera toxin B subunit and tetanus toxoid," APMIS, Jul. 1998, pp. 800-806, vol. 106.
Cepko, C. et al., "Overview of the Retrovirus Transduction System," Current Protocols in Mol. Biol., Oct. 1996, pp. 9.9.1-9.9.16, Supplement 36.
Clambey, E. et al., "Disruption of the Murine Gammaherpesvirus 68 M1 Open Reading Frame Leads to Enhanced Reactivation from Latency," J. Virol., Feb. 2000, pp. 1973-1984, vol. 74, No. 4.
Coleman, J. et al., "Virus Attenuation by Genome-Scale Changes in Codon Pair Bias," Sci., Jun. 27, 2008, pp. 1784-1787, vol. 320, No. 5884.
European Nucleotide Archive Accession EF495130.1 dated Mar. 19, 2010; 2 pgs.
Gardin, J. et al., "Measurement of average decoding rates of the 61 sense codons in vivo," eLife, 2014, pp. 1-20, vol. 3, Issue e03735.
International Search Report and Written Opinion dated Jan. 9, 2018 from related Patent Application No. PCT/US2017/050229; 13 pgs.
Lorincz, O. et al., "Structure and biological activity of pathogen-like synthetic nanomedicines," Nanomedicine: Nanotechnology, Biology, and Medicine, May 2012, pp. 497-506, vol. 8, No. 4.
Mueller, S. et al., "Reduction of the Rate of Poliovirus Protein Synthesis through Large-Scale Codon Deoptimization Causes Attenuation of Viral Virulence by Lowering Specific Infectivity," J. Virology, Oct. 2006, pp. 9687-9696, vol. 80, No. 19.
Mueller, S. et al., "Live Attenuated Influenza Vaccines by Computer-Aided Rational Design," NIH Public Access Author Manuscript, Jan. 1, 2011, pp. 1-13, published in final edited form as: Nat. Biotechnol., Jul. 2010, pp. 723-726, vol. 28, No. 7.
Paoletti, L., "Potency of clinical group B streptococcal conjugate vaccines," Vaccine, Feb. 28, 2001, pp. 2118-2126, vol. 19, Nos. 15-16.
Pavlova, I. et al., "Disruption of Gammaherpesvirus 68 Gene 50 Demonstrates that Rta Is Essential for Virus Replication," J. Virol., May 2003, pp. 5731-5739, vol. 77, No. 10.
Pavlova, I. et al., "Murine gammaherpesvirus 68 Rta-dependent activation of the gene 57 promoter," Virology, 2005, pp. 169-179, vol. 333.
Quax, T. et al "Codon Bias as a Means to Fine-Tune Gene Expression," Mol. Cell, Jul. 16, 2015, pp. 149-161, vol. 59, Elsevier Inc..
Shen, S. et al., "Large-scale recoding of an arbovirus genome to rebalance its insect versus mammalian preference," PNAS, Apr. 14, 2015, pp. 4749-4754, vol. 112, No. 15.
Speck, S. et al., "Host and viral genetics of chronic infection: a mouse model of gamma-herpesvirus pathogenesis," Curr. Opin. Microbiol., Aug. 1999, pp. 403-409, vol. 2, No. 4.
Speck, S. et al., "Viral Latency and Its Regulation: Lessons from the gamma-Herpesviruses," Cell Host Microbe, Jul. 22, 2010, pp. 100-115, vol. 8, Elsevier Inc.
Stahl, J. et al., "Amplification of JNK Signaling Is Necessary to Complete the Murine Gammaherpesvirus 68 Lytic Replication Cycle," J. Virol., Dec. 2012, pp. 13253-13262, vol. 86, No. 24.
Toke, E. et al., "Exploitation of Langerhans cells for in vivo DNA vaccine delivery into the lymph nodes," Gene Ther., 2014, pp. 1-9, Macmillan Publishers Limited.
Toke, E. et al., "Rational development of a stable liquid formulation for nanomedicine products," Inter. J. Pharmaceutics, Jun. 15, 2010, pp. 261-267, vol. 392, Nos. 1-2.
Van Dyk, L. et al., "The Murine Gammaherpesvirus 68 v-Cyclin Is a Critical Regulator of oe from Latency," J. Virol., Aug. 2000, pp. 7451-7461, vol. 74, No. 16.
Virgin, H. et al., "Complete Sequence and Genomic Analysis of Murine Gammaherpesvirus 68," J. Virol., Aug. 1997, pp. 5894-5904, vol. 71, No. 8.
Weck, K. et al., "Mature B Cells Are Required for Acute Splenic Infection, but Not for Establishment of Latency, by Murine Gammaherpesvirus 68," J. Virol., Oct. 1996, pp. 6775-6780, vol. 70, No. 10.
Wu, T-T. et al., "Function of Tra Is Essential for Lytic Replication of Murine Gammaherpesvirus 68," J. Virology, Oct. 2001, pp. 9262-9273, vol. 75, No. 19.

* cited by examiner

SEQUENCE LISTING

```
<160> NUMBER OF SEQ ID NOS: 6

<210> SEQ ID NO 1
<211> LENGTH: 1752
<212> TYPE: DNA
<213> ORGANISM: Murine Gammaherpes Virus

<400> SEQUENCE: 1
atggcctctg actcggattc cccttcagcc gataaggact ggcacggatc gaagcaggtc      60
tacttgagcc agttgattgg agtctctgct gaaacaaaag aggaatttca gcaactggta     120
gatctattta tatgcttcct acagcaccct gaagatggtt tgaatgctct gcagtatgtc     180
aagaatttgg aacttgctct tcggcgtctg cagtcagaca gtctcaaaca tgggcctttg     240
tctgggttaa tatttgacct gaacttctac aatgtctggg taatgttcag aaaccagaag     300
gtgaggttta atgccaaagt ccataacagg catccatgtg gtacatatc tcaccacctg      360 atcaaatatg ccattgaaag agttgtctat accacagaca ggctgtttct gactgcccca     420
```

```
tgttcggggg tacagctacc tcaacctctg gcctgcagtc tgttcgaaat actcaaggat        480
gttagaggaa aatgcacaac ggcctggagg cgcttagggg caggccgcag acatttaatg        540
acatttgggc gcaatgtgtt ggatgaattt aattctgaga agaagtcacc tggtggcata        600
taccagagaa gttgaggcat ttataaagat atgctttcca caaatggact aaataaaat         660 tttaattcca atttatcagc acgccatcaa catcccacca gactgtgtac ccagctgtac        720
tattggagat ggaaacagaa aacgagcccc ccacggttcg ctatacagta aagacatatc        780
ctcacaaaag ttctgcatcc cagacccct gtttgcttct cccacagaac cagggttggg         840
ggagttgcat aggggtaata tggcacattt gctgcagaac ccagaagaat cattaacctg        900
gaccctctac acaataccac tgaaccctgt ttgtatcaaa tgttttcaga ggcggtgaca        960
aacccctcta aaaaagatg ctttcttct tcaacatgg tcttttcagg actgtctccg           1020
agagctcggc cagagaccac ttatgaaacc attggggcca ttttcaccca ttcgccctgg        1080
cccttcttcc accacagaag agttccagtt tgaatttagc ccttctcctc aaacctcccc        1140
agaaacaagc gagcagagct acatacctac tcccaactca gctatgggcg gatcctttga       1200
gtacacaggc gccgttcaac cacaattaat tccagataat cacacctgtt ccgcaaagag       1260
attaagggag agcgatgagg aggtaaatta ttcttacgac ggtagtccaa caagaaacc       1320 cacagctcgc acttctgggc acgaacaggc ttatggtttt ctggccgagt tgctctctag       1380
ccacagggat acgcctgtcc agcatattgt gacctctggc tcaacgcccg ccccgccaat       1440
tgttgagcct cagggacaag attttgttgg aaaacaggat gagacatgtt ccaacgtgtt       1500
cccagaacaa attactcagg aagcgtgtcc cggatcatct gaggacgcgt tcatcgatga       1560
tgctataaag gaaatatttg catcgctgga ctctatggca aaccaggaca ctgctgacag       1620
tgacacatgt tccatacttg accccccaatc accactcccc caccctccgt tcccccaata      1680
actacactct cgttgtatga catttatgcc agcatactta gtccactcga cccaaacagc       1740
ctggagtcat aa                                                           1752

<210> SEQ ID NO 2
<211> LENGTH: 1752
<212> TYPE: DNA
<213> ORGANISM: Artificial Sequence
<220> FEATURE:
<223> OTHER INFORMATION: SYNTHESIZED

<400> SEQUENCE: 2
atggcttccg attctgactc tccctcggca gacaaagatt ggcatgggag taaacaggtt         60
tatctctctc aactaatagg tgtaagcgcc gagactaagg aagagttcca acagctcgtc        120
gacctgttta tttgtttttt gcaacatcca gaggacgggc tcaacgcctt acagtatgtt        180
aaaaacctag agttggccct gagaagactg cagtccgatt cactgaagca cggaccactt        240
agcggcctga ttttgacttt aaattttat aacgtttggg tgatgtttcg aaatcaaaaa         300
gttagattca acgctaaggt tcacaataga cacccgtgtg gatatatttc ccatcacctg        360
attaagtacg cgatagagag ggtggtatat acaactgata gattgttctt aacagcacct        420
tgttcaggag tccaattgcc acagccctta gcttgttccc ttttgagat ttgaaagacg         480 tgaggggaa gtgtactaca gcgtggcgaa gactgggagc cggtagacgg cacctgatga        540
cgtttggaag gaacgtcctc gacgagttca actccgaaaa aaaagcccca ggaggtatta       600
gtcgcgaggt cgaagccttt atcaaaatct gtttcccca gatggatctg aacaagatac        660
```

```
tgatacctat atatcaacac gctataaata taccccccga ctgcgttcca tcatgcacaa      720
taggggacgg taataggaag agggctccac atggcagctt gtattccaag gacatctctt      780
ctcagaaatt ttgtattccc gatcctttat tcgcaagccc aacggagcct ggcctaggcg      840
aacttcaccg cggcaacatg gcccaccttc tgcaaaatcc cgaagagatt ataaatctag      900
atccattgca taacactacg gagccatgcc tgtaccagat gtttagtgaa gccgtcacta      960
atccttcaaa gaagaagtgg ttgagctcat ttaatatggt ttttagtgg cttatcccct      1020
cgggccagac ccgaaacaac ctacgaaccc ctaggaccct tctctcctat atctccagga     1080
ccatcaagtg ctactgagga atttcaattc gagttttctc caagcccaca gacaagtcct     1140
gagacctcgg aacaatctta tattcccaca cctaactctg caatgggggg gtcttttgaa     1200
tatactggtg ctgtccagcc ccagttgata cccgacaacc acacttgttc tgctaaacgt     1260
ctgcgcgaat ctgacgaaga agtcaactac tcgagcgatg ggtcacccaa caaaaagcca     1320
accgccagga catcgggaca tgagcaggcc tacggatttc ttgcggaact attgagctca     1380
catagagaca caccagtgca acacatagta cagtccgggt ctacaccagc accacctatc     1440
gtcgaaccac agggtcagga cttcgtgggg aagcaggacg aaacctgctc taacgtattt     1500
cccgagcaga tcacccaaga ggcctgtcca gggtcttcag aagatgcttt tatagacgac     1560
gccatcaaag aaattttgc cagcctggac tcgatggcta atcaagatac agccgattca      1620
gatacttgct ctattctgga tccacagtcc cctacaccac cgccatcgt acctcccatt      1680
acaactttgt cactctatga catatacgca tcaattttgt ccctctgga tcctaattca      1740
ttggaatcgt aa                                                         1752

<210> SEQ ID NO 3
<211> LENGTH: 1752
<212> TYPE: DNA
<213> ORGANISM: Artificial Sequence
<220> FEATURE:
<223> OTHER INFORMATION: SYNTHESIZED

<400> SEQUENCE: 3
atggcgtcgg acagtgacag cccctctgct gacaaagatt ggcatggttc aaaacaagta       60
tatttgtctc agctcatagg tgtttcagca gagaccaagg aagagttcca gcagcttgtg      120
gacctgttca tctgtttttt gcaacatcca gaggacggcc tcaacgccct acaatatgta      180
aaaaacctag aattggcttt gagaagacta cagagtgact cgctgaagca cggcccactt      240
tcagggctga ttttgatttt aaattttat aacgtgtggg tcatgtttag aaatcaaaaa       300
gttcgcttca acgcgaaggt tcacaaccgc caccccctgcg gctatatttc acatcactta     360
ataaagtatg caatagaavg tgtggtgtac acaactgacc gcctcttta acagctccct      420
gctctggtgt ccagttgcca cagccactag catgttcttt gtttgaaatt ttgaaagacg     480
tcccggggga agtgtactac cagcttggcg caggctggga gctggaagaa ggcacctgat      540
gacttttgga agaaacgtcc tagacgaggt caactcagaa aaaaaatctc caggaggaat      600
ttcaagggag gtagaagcct tcattaaaat ttgtttcccc cagatggacc tgaacaagat      660
attgataccc atctaccaac atgcaataaa tattcctcct gattgcgtcc cttcctgcac      720
aatagggggac gggaaccgga agagggctcc acatggcagc ctgtattcca aggatatttc     780
ttctcagaaa ttttgtattc ctgatcctct cttcgcctcc ccaactgagc ctgggcttgg     840
agaactacac agaggaaaca tggcccacct gttgcaaaat cctgaggaga taataaattt     900
agatcccctg cacaacacaa cagagccatg tctctaccag atgtttagtg aagctgtcac    960
```

```
caatcccagc aagaagaggt ggttgtcctc ctttaatatg gttttagtg ggctgagccc    1020 cagggccaga cctgaaacaa cctacgagcc acttggacct tttagcccaa tttctccagg   1080
gccctcctcg gcgacggagg aatttcaatt tgagttttct cccagccccc agacgtcgcc   1140
ggagactytc agaacagtcc tatattccaa caccaaattc tgccatgggt ggttcatttg   1200
aatatactgg agctgtccag ccccagctga tacctgacaa ccatacttgt agtgccaaaa   1260
gactgagaga aagtgacgaa gaagtcaact atagctctga tggcagcccc aataaaaagc   1320
caactgccag aacatcagga catgagcagg cctacggctt tttagcagaa ttgttgtctt   1380
cacaccgaga cactccagtt caacacatag ttcagtcggg gtccacacca gctccaccca   1440
tagtagaacc acaagggcag gacttcgtgg ggaagcaaga cgaaacctgt agcaatgttt   1500
ttcctgagca gataacacaa gacgcctgcc caggttcttc agaagatgct tttattgacg   1560
accgcatcaa agagattttc gcctctttgg attccatggc caatcaagat acagcagact   1620
cagatacttg tagcatcctg gatccacagt ctccaacacc acctccttca gtacctccca   1680
tcaccacgct gtctctttat gatatatacg cctccatcct gtcgccgctg gatcccaact   1740
ctagaatctt aa                                                       1752

<210> SEQ ID NO 4
<211> LENGTH: 1752
<212> TYPE: DNA
<213> ORGANISM: Artificial Sequence
<220> FEATURE:
<223> OTHER INFORMATION: SYNTHESIZED

<400> SEQUENCE: 4
atggcttctc attctgactc tccctcggca gacaaagatt ggcatgggag taaacaggtt     60
tatctctctc aactaatagg tgtaagcgcc gagactaagg aagagttcca acagctcgtc    120
gacctgttta tttgtttttt gcaacatcca gaggacgggc tcaacgcctt acagtatgtt    180
aaaaacctag agttggccct gagaagactg cagtccgatt cactgaagca cggaccactt    240
agcggcctga tttttgactt aaattttat aacgtttggg tgatgtttcg aaatcaaaaa     300
gttagattca acgctaaggt tcacaataga cacccgtgtg gatatatttc ccatcacctg    360
attaagtacg cgatagagag ggtggtctat accacagaca ggctgtttct gactgcccca    420
tgttcggggg tacagctacc tcaacctctg gcctgcagtc tgttcgaaat actcaaggat    480
gttagaggaa aatgcacaac ggcctggagg cgcttagggg caggccgcag acatttaatg    540
acatttgggc gccatgtgtt ggatgaattt aattctgaga gaagtcacc tggtggcata     600 tccagagaag ttgaggcatt tataaagata tgctttccac aaatggactt aaataaaatt    660
ttaattccaa tttatcagca gcgcatcaac atcccaccag actgtgtacc cagctgtact    720
attggagatg gaaacagaaa acgagccccc cacggttcgc tatacagtaa agacatatcc    780
tcacaaaagt tctgcatccc agaccccctg tttgcttctc ccacagaacc agggttgggg    840
gagttgcata ggggtaatat ggcacatttg ctgcagaacc agaagaaat cattaacctg      900 gaccctctac acaataccac tgaaccctgt ttgtatcaaa tgttttcaga ggcggtgaca    960
aacccctcta aaaaagatg gctttcttct ttcaacatgg tccttttcag gactgtctcc   1020
gagagctcgg ccagagacca cttatgaaac cattggggcc attttcaccc attcgccctg    1080
gcccttcttc caccacagaa gagttccagt ttgaatttag cccttctcct caaacctccc    1140
cagaaacaag cgagcagagc tacataccta ctcccaactc agctatgggc ggatcctttg    1200
```

| | |
|---|---:|
| agtacacagg cgccgttcaa ccacaattaa ttccagataa tcacacctgt tccgcaaaga | 1260 |
| gattaaggga gagcgatgag gaggtaaatt attcttacga cggtagtcca aacaagaaac | 1320 |
| ccacagctcg cacttctggg cacgaacagg cttatggttt tctggccgag ttgctctcta | 1380 |
| gccacaggga tacgcctgtc cagcatattg tgacctctgg ctcaacgccc gccccgccaa | 1440 |
| ttgttgagcc tcagggacaa gattttgttg gaaaacagga tgagacatgt tccaacgtgt | 1500 |
| tcccagaaca aattactcag gaagcgtgtc ccggatcatc tgaggacgcg ttcatcgatg | 1560 |
| atgctataaa ggaaatattt gcatcgctgg actctatggc aaaccaggac actgctgaca | 1620 |
| gtgacacatg ttccatactt gaccccccaat caccactccc ccaccctccg ttcccccaat | 1680 |
| aactacactc tcgttgtatg acatttatgc cagcatactt agtccactcg acccaaacag | 1740 |
| ccggagtcat aa | 1752 |

<210> SEQ ID NO 5
<211> LENGTH: 1752
<212> TYPE: DNA
<213> ORGANISM: Artificial Sequence
<220> FEATURE:
<223> OTHER INFORMATION: SYNTHESIZED

<400> SEQUENCE: 5

| | |
|---|---:|
| atggcttcta attctgactc tccttctgct gacaaagatt ggcatgggtc caagcaagta | 60 |
| tacctgtcgc agctaatagg tgtctcggcc gagacaaagg aagaattcca gcagttggtc | 120 |
| gacctgttca tatgttttct gcagcatcca gaagacgggc tcaacgcctt acagtacgta | 180 |
| aaaaatctag aattggccct gcggaggctt cagagtgatt cttttgaagca cggacctctt | 240 |
| tcagggctga ttttgatttt gaattttac aacgtgtggg tcatgtttag aaatcagaaa | 300 |
| gtccgtttca acgctaaggt ccacaataga caccccttgcg gatatataag ccatcacttg | 360 |
| atcaaatatg ccattgaaag agttgtctat accacagaca ggctgtttct gactgcccca | 420 |
| tgttcggggg tacagctacc tcaacctctg gcctgcagtc tgttcgaaat actcaaggat | 480 |
| gttagaggaa aatgcacaac ggcctggagg cgcttagggg caggccgcag acatttaatg | 540 |
| acatttgggc gccatgtgtt ggatgaattt aattctgaga agaagtcacc tggtggcata | 600 |
| tccagagaag ttgaggcatt tataaagata tgcttttccac aaatggactt aaataaaatt | 660 |
| ttaattccaa tttatcagca gcgcatcaac atcccaccag actgtgtacc cagctgtact | 720 |
| attggagatg gaaacagaaa acgagccccc cacggttcgc tatacagtaa agacatatcc | 780 |
| tcacaaaagt tctgcatccc agaccccctg tttgcttctc ccacagaacc agggttgggg | 840 |
| gagttgcata ggggtaatat ggcacatttg ctgcagaacc cagaagaaat cattaacctg | 900 |
| gaccctctac acaataccac tgaaccctgt ttgtatcaaa tgttttcaga ggcggtgaca | 960 |
| aacccctcta aaaaagatg gctttcttct ttcaacatgg tccttttcag gactgtctcc | 1020 |
| gagagctcgg ccagagacca cttatgaaac cattggggcc attttcaccc attcgccctg | 1080 |
| gcccttcttc caccacagaa gagttccagt ttgaatttag cccttctcct caaacctccc | 1140 |
| cagaaacaag cgagcagagc tacatacccta ctcccaactc agctatgggc ggatcctttg | 1200 |
| agtacacagg cgccgttcaa ccacaattaa ttccagataa tcacacctgt tccgcaaaga | 1260 |
| gattaaggga gagcgatgag gaggtaaatt attcttacga cggtagtcca aacaagaaac | 1320 |
| ccacagctcg cacttctggg cacgaacagg cttatggttt tctggccgag ttgctctcta | 1380 |
| gccacaggga tacgcctgtc cagcatattg tgacctctgg ctcaacgccc gccccgccaa | 1440 |
| ttgttgagcc tcagggacaa gattttgttg gaaaacagga tgagacatgt tccaacgtgt | 1500 |

| | |
|---|---:|
| tcccagaaca aattactcag gaagcgtgtc ccggatcatc tgaggacgcg ttcatcgatg | 1560 |
| atgctataaa ggaaatattt gcatcgctgg actctatggc aaaccaggac actgctgaca | 1620 |
| gtgacacatg ttccatactt gacccccaat caccactccc ccaccctccg ttcccccaat | 1680 |
| aactacactc tcgttgtatg acatttatgc cagcatactt agtccactcg acccaaacag | 1740 |
| ccggagtcat aa | 1752 |

<210> SEQ ID NO 6
<211> LENGTH: 1752
<212> TYPE: DNA
<213> ORGANISM: Artificial Sequence
<220> FEATURE:
<223> OTHER INFORMATION: SYNTHESIZED

<400> SEQUENCE: 6

| | |
|---|---:|
| atggcctcgg acagtgacag cccctctgct gacaaagatt ggcatggttc aaaacaagta | 60 |
| tatttgtctc agctcatagg tgtttcagca gagaccaagg aagagttcca gcagcttgtg | 120 |
| gacctgttca tctgtttttt gcaacatcca gaggacggcc tcaacgccct acaatatgta | 180 |
| aaaaacctag aattggcttt gagaagacta cagagtgact cgctgaagca cggcccactt | 240 |
| tcagggctga ttttgatttt aaattttttat aacgtgtggg tcatgtttag gaatcaaaaa | 300 |
| gttcgcttca acgcgaaggt tcacaaccgc caccccgtcg gctatatttc acatcactta | 360 |
| ataaagtatg caatagaacg tgtggtctat accacagaca ggctgtttct gactgcccca | 420 |
| tgttcggggg tacagctacc tcaacctctg gcctgcagtc tgttcgaaat actcaaggat | 480 |
| gttagaggaa aatgcacaac ggcctggagg cgcttagggg caggccgcag acatttaatg | 540 |
| acatttgggc gccatgtgtt ggatgaattt aattctgaga agaagtcacc tggtggcata | 600 |
| tccagagaag ttgaggcatt tataaagata tgctttccac aaatggactt aaataaaatt | 660 |
| ttaattccaa tttatcagca gcgcatcaac atcccaccag actgtgtacc cagctgtact | 720 |
| attggagatg gaaacagaaa acgagccccc cacggttcgc tatacagtaa agacatatcc | 780 |
| tcacaaaagt tctgcatccc agacccctg tttgcttctc ccacagaacc agggttgggg | 840 |
| gagttgcata ggggtaatat ggcacatttg ctgcagaacc cagaagaaat cattaacctg | 900 |
| gaccctctac acaataccac tgaaccctgt ttgtatcaaa tgttttcaga ggcggtgaca | 960 |
| aaccctctta aaaaagatg gctttcttct ttcaacatgg tccttttcag gactgtctcc | 1020 |
| gagagctcgg ccagagacca cttatgaaac cattggggcc attttcaccc attcgccctg | 1080 |
| gcccttcttc caccacagaa gagttccagt ttgaatttag ccttctcctc aaacctccc | 1140 |
| cagaaacaag cgagcagagc tacataccta ctcccaactc agctatgggc ggatcctttg | 1200 |
| agtacacagg cgccgttcaa ccacaattaa ttccagataa tcacacctgt tccgcaagaa | 1260 |
| gattaaggga gagcgatgag gaggtaaatt attcttacga cggtagtcca aacaagaaac | 1320 |
| ccacagctcg cacttctggg cacgaacagg cttatggttt tctggccgag ttgctctcta | 1380 |
| gccacaggga tacgcctgtc cagcatattg tgacctctgg ctcaacgccc gccccgccaa | 1440 |
| ttgttgagcc tcagggacaa gattttgttg gaaaacagga tgagacatgt tccaacgtgt | 1500 |
| tcccagaaca aattactcag gaagcgtgtc ccggatcatc tgaggacgcg ttcatcgatg | 1560 |
| atgctataaa ggaaatattt gcatcgctgg actctatggc aaaccaggac actgctgaca | 1620 |
| gtgacacatg ttccatactt gacccccaat caccactccc ccaccctccg ttcccccaat | 1680 |

```
aactacactc tcgttgtatg acatttatgc cagcatactt agtccactcg acccaaacag    1740
ccggagtcat aa                                                       1752
```

COMPOSITIONS AND METHODS FOR GENERATING REVERSION FREE ATTENUATED AND/OR REPLICATION INCOMPETENT VACCINE VECTORS

CROSS REFERENCE TO RELATED APPLICATIONS

This application claims the benefit of International Patent Application number PCT/US2017/050229, filed Sep. 6, 2017, which claims the benefit of U.S. Provisional Application No. 62/383,907, filed Sep. 6, 2016, the disclosures of which are hereby incorporated by reference in their entirety.

GOVERNMENTAL RIGHTS

This invention was made with government support under CA167065 awarded by the National Institute of Health. The government has certain rights in the invention.

FIELD OF THE INVENTION

The disclosure provides methods for generating reversion free attenuated and/or replication incompetent vaccine vectors and their use in vaccine compositions and vaccination.

BACKGROUND OF THE INVENTION

DNA viruses are highly recombinogenic which makes complementation of attenuated and replication defective viral mutants by traditional approaches difficult due to the high likelihood of reversion to wild-type (WT) non-mutant sequence. Complementation is typically performed by developing cell lines in which wild-type copies of mutant genes are maintained. Unfortunately, this approach often leads to wild-type reversion which is thought to occur primarily by homologous recombination between complementation constructs and mutant viral genomes due to the high number of identical nucleotide sequences present in complementation constructs and mutant viral genomes. Thus, there is a need in the art for a method of making vaccine compositions that do not revert to wild-type, fully virulent viruses.

BRIEF DESCRIPTION OF THE FIGURES

The application file contains at least one drawing executed in color. Copies of this patent application publication with color drawing(s) will be provided by the Office upon request and payment of the necessary fee.

Figure 1A:
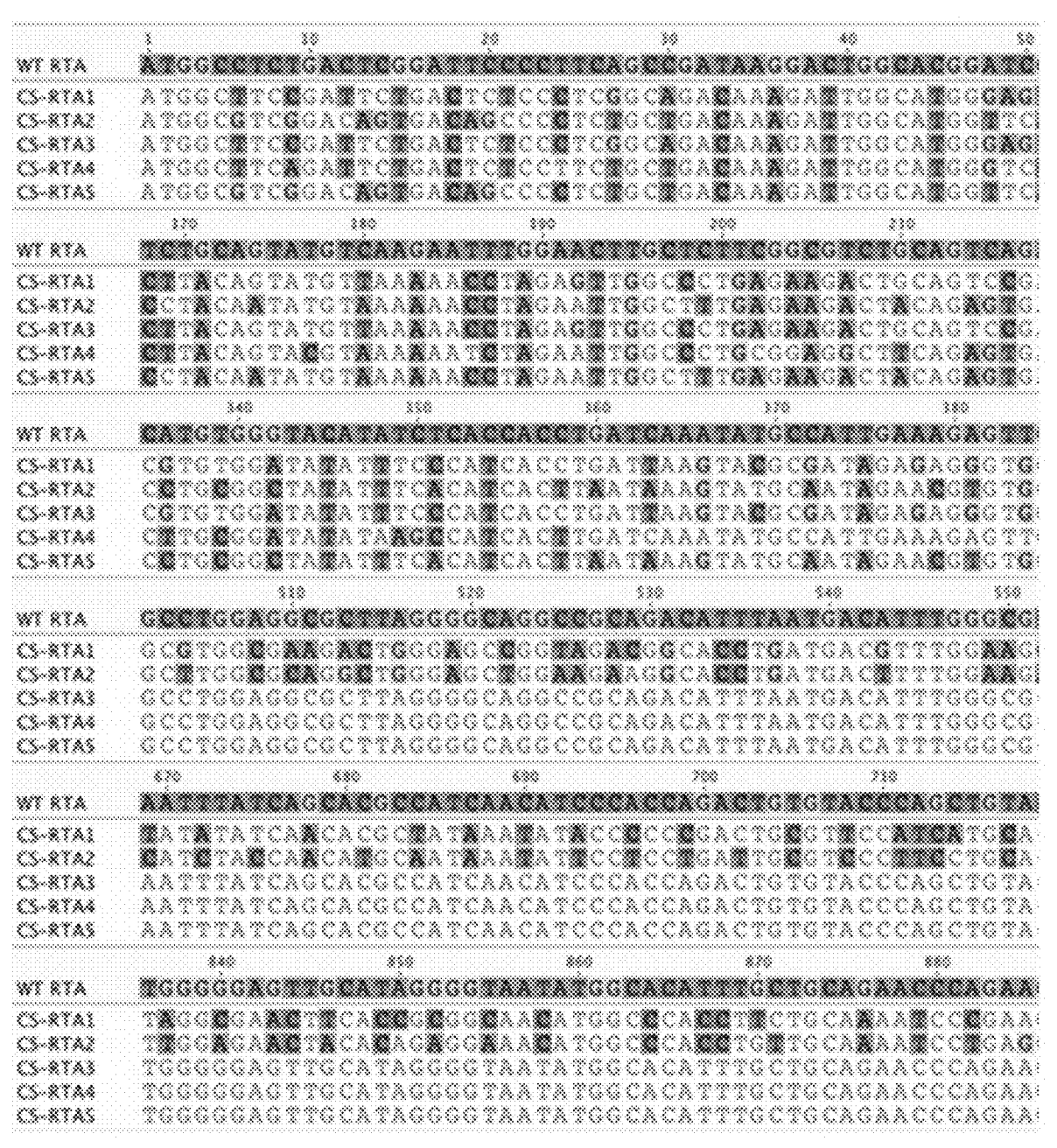
Figure 1B:
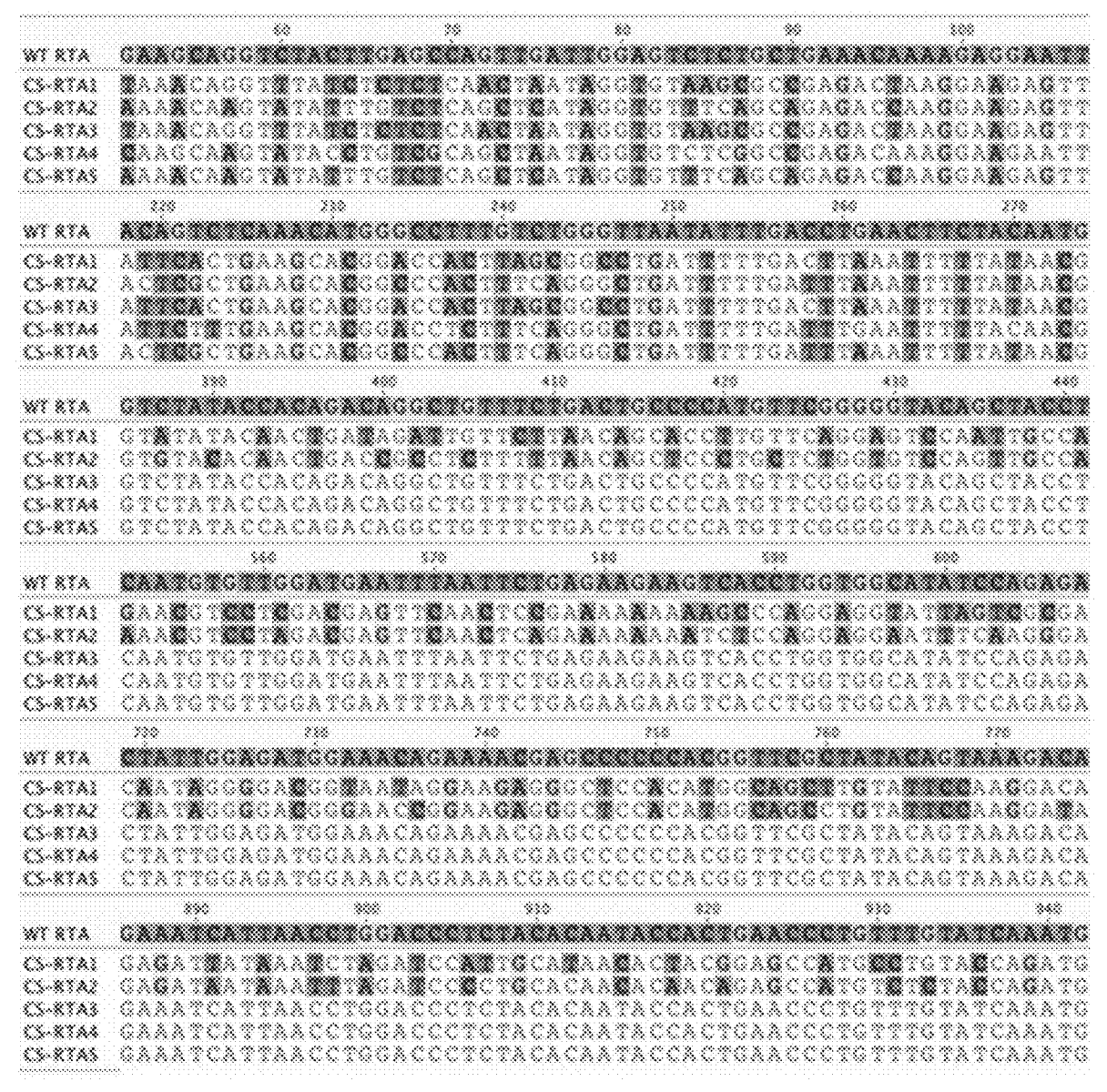
Figure 1C:
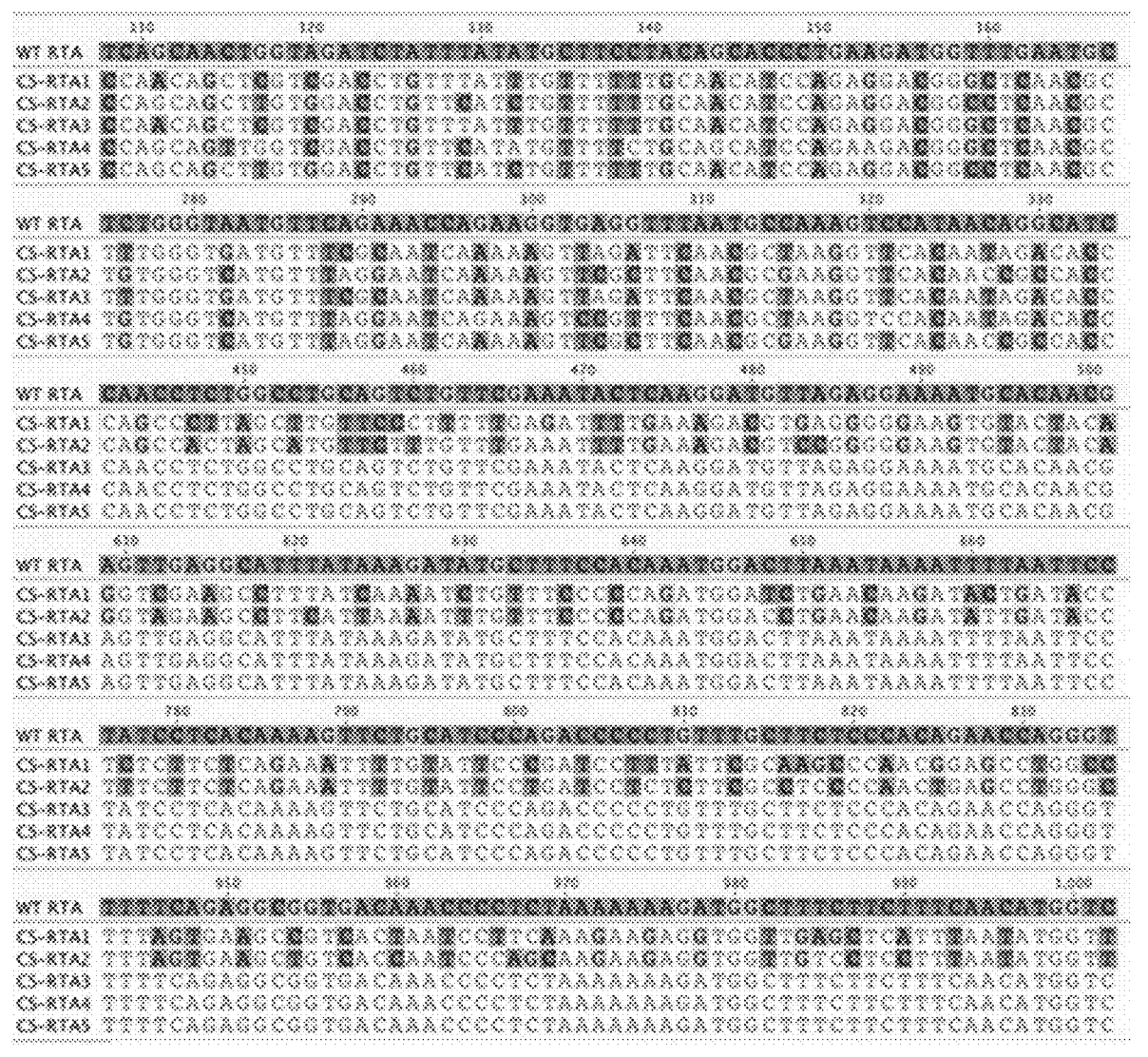
Figure 1D:
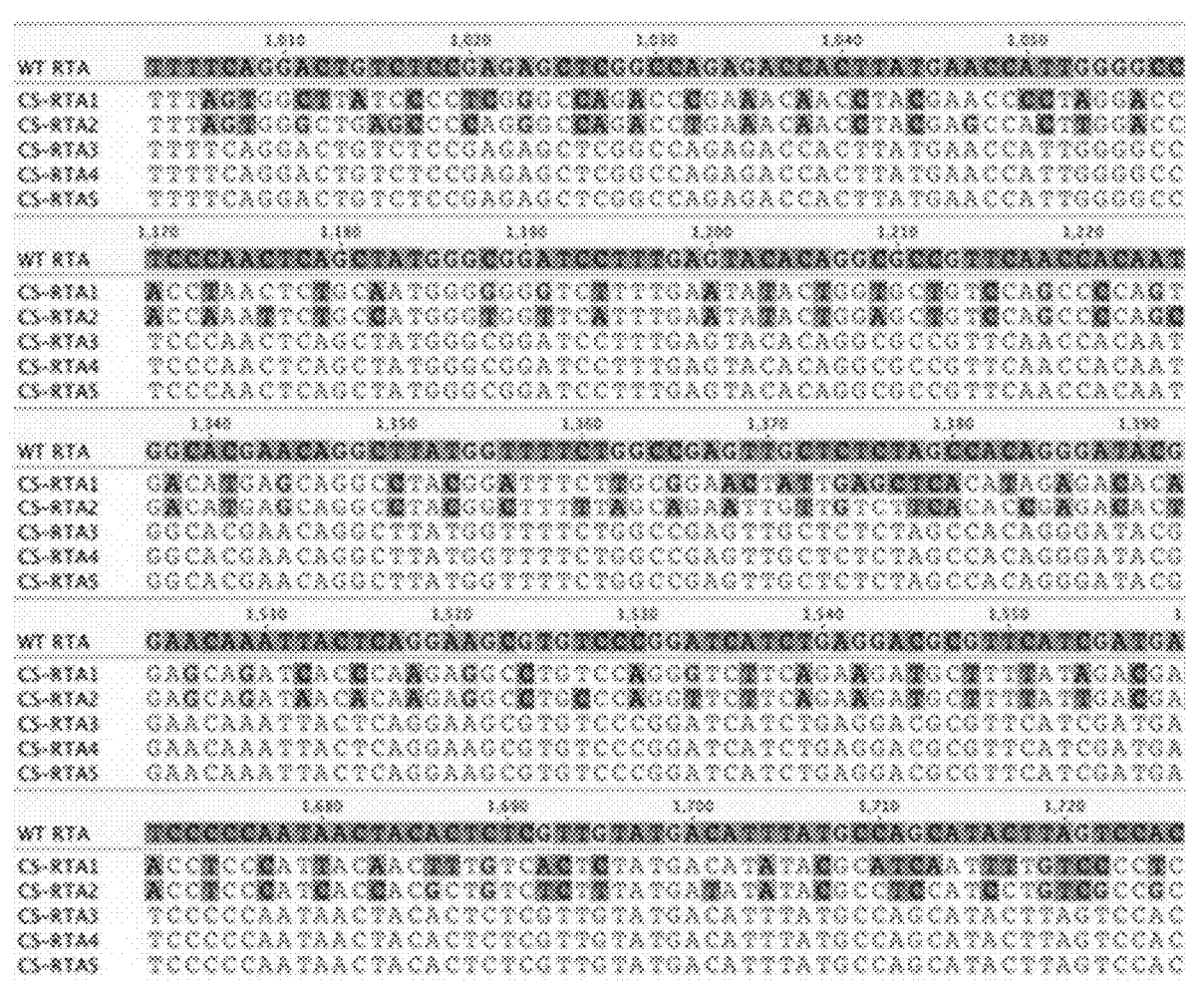
Figure 1E:
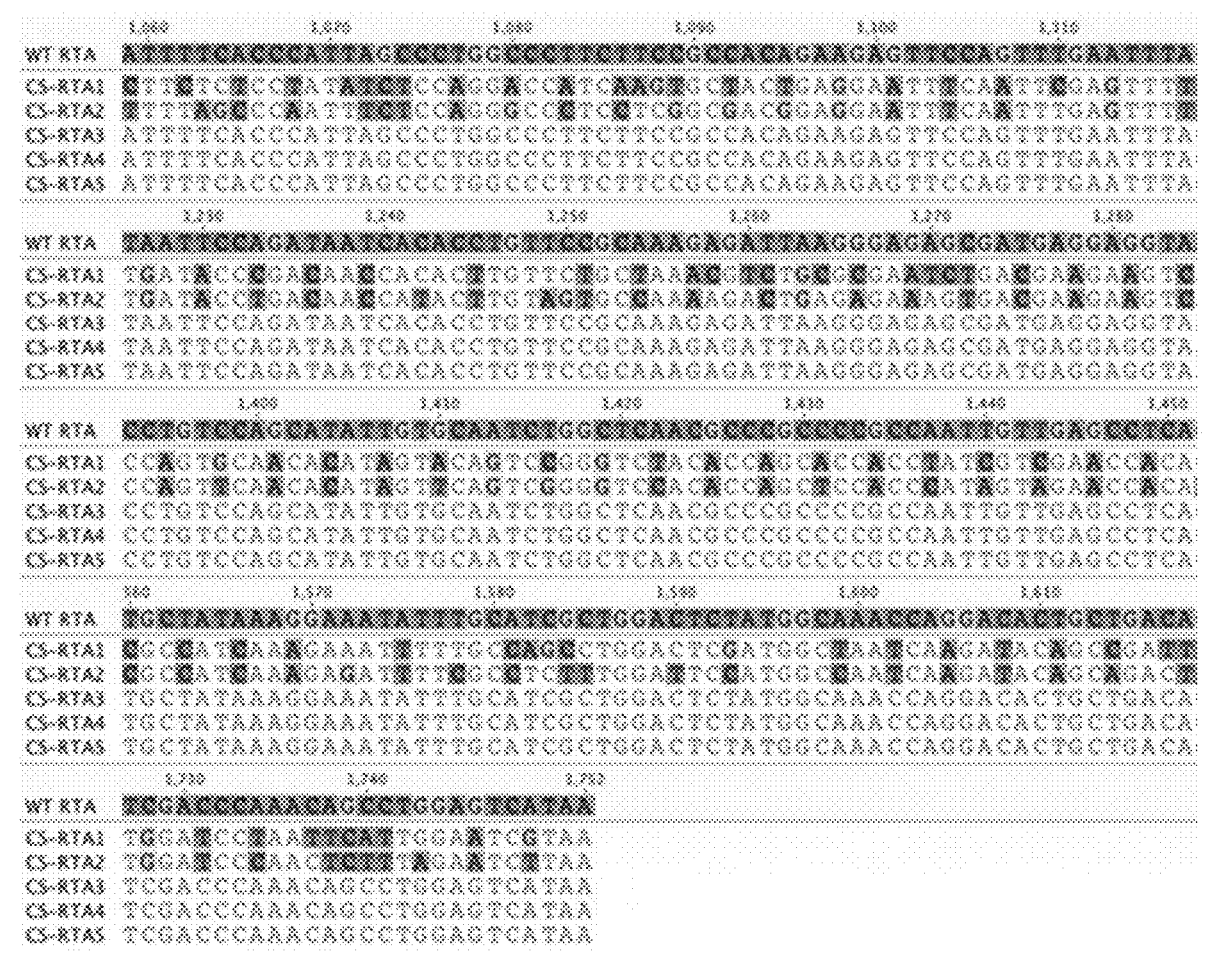
Figure 1F:
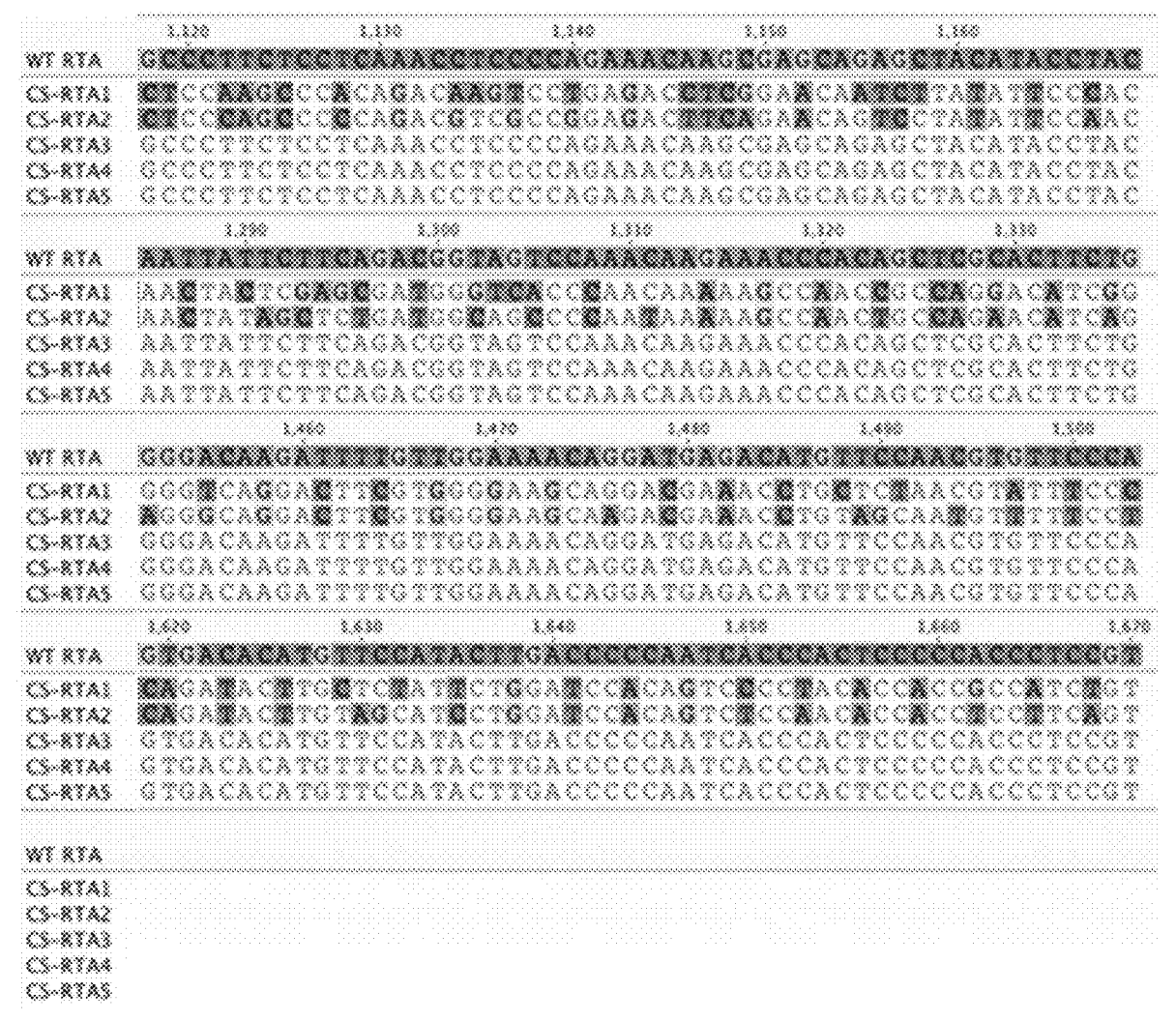

FIG. 1 depicts nucleotide alignments of codon-shuffled ORF50 sequences with WT-MHV68 ORF50. Synthetic RTA-encoding ORF50 nucleotide sequences were derived using computer algorithms that take into account codon adaptation index and codon pair bias scores. Absolute codon content is preserved in the codon shuffling approach, while nucleotide sequences and thus nucleotide homology are disrupted. Shown are alignments of synthetic CS-RTA nucleotide sequences produced for this study with WT-MHV68 ORF50. WT-RTA (SEQ ID NO:1), CS-RTA1 (SEQ ID NO:2), CS-RTA2 (SEQ ID NO:3), CS-RTA3 (SEQ ID NO:4), CS-RTA4 (SEQ ID NO:5), and CS-RTA5 (SEQ ID NO:6).

(FIG. 2A) 293T cells were transfected with plasmids encoding the indicated constructs appended with a FLAG epitope tag. Cells were lysed and proteins were resolved by SDS-PAGE 24 h after transfection. Immunoblot analyses using FLAG-specific antibodies were performed to evaluate expression of WT-RTA and CS-RTAs. Detection of beta-actin serves as a loading control. (FIG. 2B, FIG. 2C) 293T cells were transfected with plasmids encoding the indicated constructs in the presence of firefly luciferase reporter plasmids containing RTA-responsive promoter sequences for gene ORF57 (FIG. 2B) or gene ORF72 (FIG. 2C). Cells were harvested 24 h post-transfection, and luciferase activity in lysates was determined in a luminometer. Experiments were normalized for variation in transfection efficiency by co-transfection with a constitutively-active *renilla* luciferase reporter plasmid. Values indicate RTA-mediated induction of the viral promoters as a firefly/*renilla* signal ratio. Values represent means of three independent experiments. Error bars represent standard deviations.

(FIG. 3A) After selection with puromycin, cells were fixed and stained with FLAG-specific antibodies, and protein expression and localization were visualized by indirect immunofluorescence microscopy. DNA was visualized by staining with DAPI. (FIG. 3B) Stable cell lines were lysed and proteins were resolved by SDS-PAGE. Immunoblot analyses using FLAG-specific antibodies were performed to evaluate expression of WT-RTA and CS-RTAs. Detection of beta-actin serves as a loading control.

(FIG. 5A) Vector control, WT-RTA or CS-RTA stable cell lines were transfected with either wild-type MHV68 BAC or ORF50.STOP MHV68 BAC, and viral stocks were produced. Viral titers for each stock were determined by plaque assay on either WT-RTA (FIG. 5A) or vector control (FIG. 5B) stable cell lines. Results are means of triplicate samples. Error bars represent standard deviations. (FIG. 5C) Representative phase contrast and epifluorescence microscopic images demonstrating sporadic GFP-positive cells (see lower right panel) indicative of non-spreading infection by RTA-null virus produced in CS-RTA cells.

FIG. 6A, FIG. 6B and FIG. 6C depicts images showing that CS-RTA prevents wild-type reversion during complementation of RTA-null MHV68. (FIG. 6A) RTA-null MHV68 produced in either WT-RTA or CS-RTA4 3T12 stable cell lines and concentrated to greater than $10^8$ PFU/ml was plated directly onto vector control cells in a plaque assay to test for the presence of wild-type revertant virus in stocks. (FIG. 6B) Undiluted RTA-null virus stocks were plated onto vector control 3T12s and observed for cytopathic effect. This assay is approximately 10-fold more sensitive at detecting replication competent virus than standard plaque assays. (FIG. 6C) Plaque assay on WT RTA expressing cell lines demonstrating approximately equivalent complemented viral titers for RTA-null virus stocks produced in either WT RTA or CS-RTA4 cells used in FIG. 6A and FIG. 6B.

DETAILED DESCRIPTION OF THE INVENTION

Figure 2A:
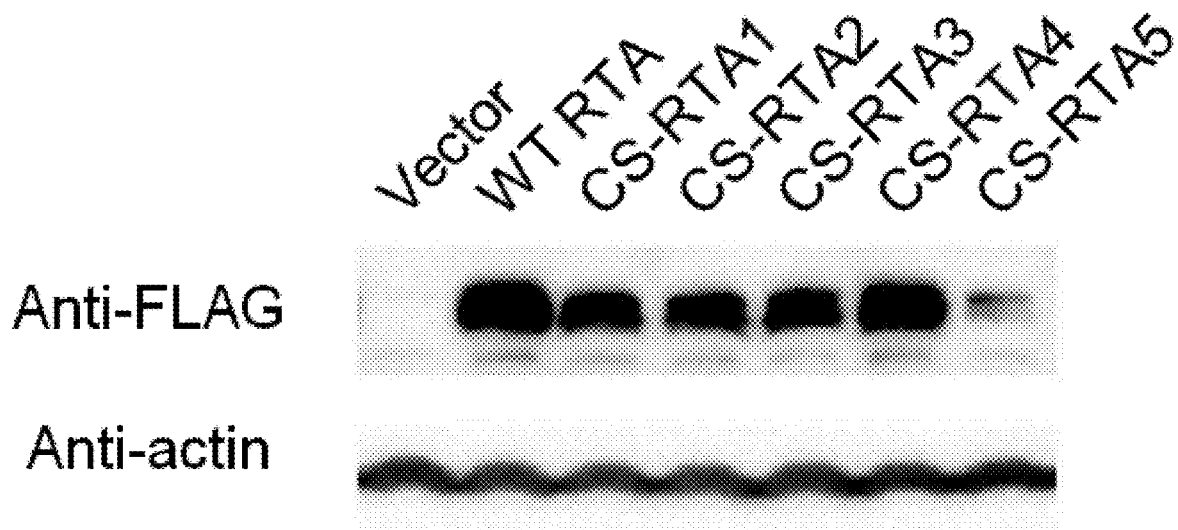
FIG. 2A, FIG. 2B and FIG. 2C depicts an immunoblot and graphs showing CS-RTA constructs are translated and functional.

Provided herein are methods of preventing or reducing viral reversion of a virus during culture. These methods allow for the production of viral stocks useful in vaccine compositions without risk of reverting to wild-type, virulent viruses. Codon shuffling was used to design helper genes in which the DNA sequence, but not encoded amino acid sequence, was altered. These codon shuffled helper genes were used to make stable cell lines for complementing a replication defective virus. The goal of this approach was to alter the DNA composition in such a manner that homology between the helper gene and viral DNA were minimized, thus limiting potential for homologous recombination. Upon employing this approach to generate complemented, high-titer stocks of a recombinant virus, wild-type reversion viruses were not detected. This approach provides a platform for the development of safe attenuated and replication-incompetent DNA virus vaccines in which codon shuffled helper gene complementation is used to enable industrial scale production of vaccine stocks with minimal to no risk of wild-type reversion. The approach also provides an improved means for generating replication incompetent gene therapy vectors. Further, codon shuffling may be used to enhance expression of helper genes thereby facilitating derivation of vaccine or gene therapy virus stocks. Still further, as it is not possible to make "particle" vaccines for herpesvirus, the method disclosed herein may be used to make vaccine stocks for herpesviruses ensuring that the vaccine stocks are devoid of revertant wild-type, virulent viruses.

I. Method of Culturing

In an aspect, the disclosure provides a method of preventing or reducing wild-type reversion of a mutant virus during culture. The method comprises stably expressing a codon shuffled helper gene in a host cell and culturing the host cell under conditions conducive to the propagation of a replication incompetent virus.

A "virus" is an infectious agent that consists of protein and nucleic acid, and that uses a host cell's genetic machinery to produce viral products specified by the viral nucleic acid. A "nucleic acid" refers to a polymer of DNA or RNA that is single or double-stranded, linear or circular, and, optionally, contains synthetic, non-natural, or modified nucleotides, which are capable of being incorporated into DNA or RNA polymers. A DNA polynucleotide preferably is comprised of genomic or cDNA sequences. A virus may be a RNA virus or a DNA virus. In a specific embodiment, a virus is a DNA virus. A DNA virus may be any virus within the families of DNA viruses including, but not limited to, Myoviridae, Podoviridae, Siphoviridae, Alloherpesviridae, Herpesviridae (e.g. human herpesviruses, varicella zoster virus), Malacoherpesviridae, Lipothrixviridae, Rudiviridae, Adenoviridae (e.g. human adenoviruses), Ampullaviridae, Ascoviridae, Asfarviridae (e.g. African swine fever virus), Baculoviridae, Bicaudaviridae, Clavaviridae, Corticoviridae, Fuselloviridae, Globuloviridae, Gutta viridae, Hytrosaviridae, Iridoviridae, Marseilleviridae, Mimiviridae, Nudiviridae, Nimaviridae, Pandora viridae, Papilloma viridae, Phycodnaviridae, Plasma viridae, Polydnaviruses, Polyomaviridae (e.g. Simian virus 40, JC virus, BK virus), Poxviridae (e.g. cowpox virus, smallpox), Sphaerolipoviridae, Tectiviridae, Turriviridae, Anelloviridae, Bacillariodnaviridae, Bidnaviridae, Circoviridae, Geminiviridae, Inoviridae, Microviridae, Nanoviridae, Parvoviridae, and Spiraviridae. The DNA virus may be selected from the group consisting of a herpes simplex virus-1, a herpes simplex virus-2, a varicella zoster virus, an Epstein-Barr virus, a cytomegalovirus, a roseolovirus, a Kaposi sarcoma-associated herpesvirus, an adenovirus, a polyomavirus, a smallpox virus (variola), a vaccinia virus, a cowpox virus, a monkeypox virus, and a papillomavirus. In an embodiment, the DNA virus may be selected from the group consisting of a herpes simplex virus-1, a herpes simplex virus-2, a varicella zoster virus, an Epstein-Barr virus, a cytomegalovirus, a roseolovirus, a Kaposi sarcoma-associated herpesvirus, an adenovirus, a polyomavirus, and a papillomavirus. In a specific embodiment, a DNA virus is a herpesvirus. A herpesvirus can be an alpha, beta or gamma herpesvirus. In one specific embodiment, a herpesvirus is a gammaherpesvirus. Additionally, a virus can also be a virus typically used as a gene therapy vector. Non-limiting examples of viruses typically used as gene therapy vectors include adenoviruses, adeno-associated viruses, herpes simplex viruses, SV-40 viruses, papillomaviruses, Epstein-Barr viruses, and vaccinia viruses. Specifically, a virus for gene therapy is selected from the group consisting of an adenovirus, an adeno-associated virus, and a herpes simplex virus. Still further, a virus can also be a virus typically used as an oncolytic virus. Non-limiting examples of viruses typical used as an oncolytic virus include adenovirus, reovirus, measles, herpes simplex, Newcastle disease virus and vaccinia. The oncolytic virus may be engineered for tumor selectivity. By way of non-limiting example, a virus may infect vertebrates, plants, insects, bacteria, protozoa, crustaceans, mollicutes, and amoebae.

A "wild-type strain of a virus" is a strain that does not comprise any of the human-made mutations as described herein, i.e., any virus that can be isolated from nature. Alternatively, a wild-type strain is any virus that has been cultured in a laboratory, but still, in the absence of any other virus or helper gene, is capable of producing progeny genomes or virions like those isolated from nature.

A "replication incompetent virus" is not a wild-type strain of a virus, inasmuch as it comprises human-made mutations or modifications. Thus, the replication incompetent virus typically is derived from a wild-type viral strain by genetic manipulation (i.e., by deletion) to generate a replication incompetent virus. The replication incompetent virus contains any combination of structural protein sequences, enzymatic protein sequences, and/or envelope protein sequences but lacks one or more genes essential for virion progeny production and/or one or more genes essential genes for production of infectious progeny. For example, the replication incompetent virus may be able to produce progeny virions, but the progeny virions are not infectious to the host cell. Accordingly, the replication incompetent virus is attenuated. Thus, a replication incompetent virus cannot complete its replicative cycle in a host cell without complementation by one or more helper gene(s) or a replication incompetent virus can complete its replicative cycle in a host cell but is not infectious to another host cell without complementation by one or more helper gene(s). In rare instances, the replication incompetent virus may be able to replicate, but not replicate to appreciable levels. Preferably, the replication incompetent virus requires complementation with one or more helper gene(s) from the wild-type virus in order to replicate to sufficient levels or the replication incompetent virus requires complementation with one or more helper gene(s) from the wild-type virus in order to infect host cells. Thus, a replication incompetent virus according to the disclosure is a virus that replicates in a host cell only upon complementation with a helper gene or is a virus that infects a host cell only upon complementation with a helper gene. Stated another way, a replication incompetent virus may be attenuated.

A "host cell" is a cell capable of being infected with a wild-type strain of virus. Additionally, a host cell is one that comprises a vector encoding one or more helper gene(s) necessary for virion progeny production or one or more helper gene(s) for production of infectious progeny. A host cell is characterized in that after transduction with a helper vector (described below), it produces the desired helper gene product. A host cell can be any cell, and, preferably, is a eukaryotic cell. A host cell can be present as a single entity, or can be part of a larger collection of cells. Such a larger collection of cells can comprise, for instance, a cell culture (either mixed or pure), a tissue, an organ, an organ system, or an organism. In certain embodiments, a host cell may be an established, commercially-available cell line (e.g., American Type Culture Collection (ATCC), Manassas, Va.). Non-limiting examples of cell lines may be found at atcc.org. In an embodiment, a host cell is a fibroblast cell line. In a specific embodiment, a host cell is a 3T12 fibroblast cell line. A host cell may be an immortalized cell. Alternatively, a host cell may be a primary cell. "Primary cells" are cells taken directly from living tissue (i.e. biopsy material) and established for growth in vitro, that have undergone very few population doublings and are therefore more representative of the main functional components and characteristics of tissues from which they are derived, in comparison to continuous tumorigenic or artificially immortalized cell lines.

A "helper vector" may be used interchangeably with a "vector encoding one or more helper gene(s)". With respect to the helper vector, its expression can be cell specific or not cell-specific and it can be introduced into a host cell in concert with a replication incompetent virus and, thereby, enable continuous replication of the replication incompetent virus.

A helper vector of the disclosure supplies one or more necessary gene product(s) for replication. A helper vector can refer to either a single vector or multiple vectors. In one specific embodiment, a helper vector is a single vector. Data generated by the inventors indicates that a helper vector must be introduced into the host cell via retroviral transduction. Use of a retrovirus vector rather than a plasmid vector results in much lower reversion rates. A retrovirus vector is an infectious virus used to introduce one or more helper gene(s) into a host cell. Originating from replication-competent viruses isolated from rodents or chickens, the vectors are modified in various ways to serve in the transduction process. The efficient and precise integration machinery of naturally occurring retroviruses is utilized to produce either a single copy or a few copies of the viral genome stably integrated into a host cell chromosome. Retroviral vectors are useful in achieving stable and efficient transduction of one or more helper gene(s) into host cells. A selectable marker may be included on the helper vector to select for cells that stably express the helper gene. A selectable marker may be used to efficiently select and identify cells that have integrated the helper gene. Selectable markers give the cell receiving the helper gene a selection advantage, such as resistance towards a certain toxin or antibiotic. Suitable examples of antibiotic resistance markers include, but are not limited to, those coding for proteins that impart resistance to kanamycin, spectomycin, neomycin, gentamycin (G418), ampicillin, tetracycline, chloramphenicol, puromycin, hygromycin, zeocin, and blasticidin. Methods of retroviral transduction are known in the art. For example, see Cepko and Pear, *Current Protocols in Molecular Biology* (1996) 9.9.1-9.9.16, the disclosure of which is hereby incorporated by reference in its entirety. A variety of retroviruses are suitable for use. The retroviral vector may be a murine stem cell virus, an alpharetrovirus, a betaretrovirus, a gammaretrovirus, a deltaretrovirus, an epsilonretrovirus, a lentivirus, or a spumaretrovirus. In a specific embodiment, the retroviral vector is a murine stem cell virus. In another specific embodiment, a helper vector is introduced into a host cell via retroviral transduction with a murine stem cell virus. In an embodiment, the retroviral vector may be a lentiviral vector. The lentiviral vector may be derived from human, simian, feline, equine, bovine, or lentiviruses that infect other mammalian species. Non-limiting examples of suitable lentiviruses includes human immunodeficiency virus (HIV), simian immunodeficiency virus (SIV), feline immunodeficiency virus (FIV), bovine immunodeficiency virus (BIV), and equine infectious anemia virus (EIAV). In a specific embodiment, the host cell is stably transfected with a helper gene via a murine stem cell virus.

As used herein, "complementation" refers to the non-genetic interaction of viral gene products from different sources in cells. Specifically, complementation comprises an enhancement in the viral yield of the replication incompetent virus or an enhancement in viral infectivity of the replication incompetent virus, while the genotype of the replication incompetent virus remains unchanged. More specifically, complementation with one or more helper gene(s) results in the enhancement in the viral yield of the replication incompetent virus or an enhancement in viral infectivity of the replication incompetent virus, while the genotype of the replication incompetent virus remains unchanged.

In order to achieve successful complementation in a system that utilizes a helper vector in conjunction with the replication incompetent virus, any viral component necessary for viral packaging and/or infectivity but not expressed from the replication incompetent virus must be provided by the helper vector. Thus, as long as the helper vector and replication incompetent virus together possess a full complement of necessary viral components, the composition of the helper vector and the mutation present in the replication incompetent virus is subject to many permutations. Each of these permutations is encompassed within the present disclosure. As used herein a "helper gene" is defined as a regulatory gene, DNA replication gene, and/or structural gene necessary for successful viral gene expression, viral DNA replication and/or virion production. As an example, a regulatory gene, DNA replication gene, and/or structural gene necessary for successful viral gene expression, viral DNA replication and/or virion production, respectively, may be incorporated in the helper vector and the regulatory gene, DNA replication gene, and/or structural gene, respectively, may be deleted from the replication incompetent virus. Non-limiting examples of genes that may be deleted from the replication incompetent virus include ORF6 (single-stranded DNA binding protein), ORF7 (Transport protein), ORF8 (Glycoprotein B), ORF9 (viral DNA polymerase), ORF17 (Capsid protein), ORF18, ORF19 (Tegument protein), ORF21 (thymidine kinase), ORF22 (Glycoprotein H), ORF24, ORF25 (Major capsid protein), ORF26 (Capsid protein), ORF27, ORF29b (Packaging protein), ORF29a (Packaging protein), ORF31, ORF32, ORF33, ORF34, ORF35, ORF36 (viral kinase), ORF37 (alkaline exonuclease), ORF39 (glycoprotein M), ORF40 (helicase-primase), ORF42, ORF43 (Capsid protein), ORF44 (Helicase-primase), ORF45, ORF46 (Uracil DNA glycosylase), ORF48 (Glycoprotein L), ORF49, ORF50 (Replication and transcription activator), ORF52, ORF53, ORF54 (dUTPase), ORF55, ORF56 (DNA replication protein), M8, ORF57 (mRNA transcript accumulation protein), ORF59 (DNA replication protein), ORF60 (Ribonucleotide reductase, small), ORF61 (Ribonucleotide reductase, large), ORF62 (Assembly/DNA maturation), ORF63 (Tegument protein), ORF64 (Tegument protein), ORF65/M9 (Glycoprotein), ORF66, ORF67 (Tegument protein), ORF68 (Glycoprotein), ORF69, ORF73 (latency-associated nuclear antigen), and ORF75c (Tegument protein/FGARAT). In certain embodiments, genes that may be deleted from the replication incompetent virus include ORF6 (single-stranded DNA binding protein), ORF7 (Transport protein), ORF8 (Glycoprotein B), ORF9 (viral DNA polymerase), ORF17 (Capsid protein), ORF19 (Tegument protein), ORF21 (thymidine kinase), ORF22 (Glycoprotein H), ORF25 (Major capsid protein), ORF26 (Capsid protein), ORF29b (Packaging protein), ORF29a (Packaging protein), ORF43 (Capsid protein), ORF44 (Helicase-primase), ORF56 (DNA replication protein), ORF59 (DNA replication protein), ORF64 (Tegument protein), ORF68 (Glycoprotein), and ORF69. Specifically, the ORF50 (replication and transcriptional activator, RTA) gene may be incorporated in the helper vector and the ORF50 gene may be deleted from the replication incompetent virus.

The nucleotide sequence of the helper gene is modified or mutagenized in order to decrease the chance for recombination with the replication incompetent virus. Accordingly, the nucleotide sequence of the helper gene has small enough homology such that it does not recombine with the replication incompetent virus. Recombination may be prevented via codon shuffling while maintaining distribution or sequence scrambling to maximize dissimilarity while maintaining codon sequence. More specifically, the nucleotide sequence of the helper gene is codon shuffled to limit or remove regions of homology between the replication incompetent virus and the helper gene. Codon shuffling alters the nucleotide sequence of the wild-type helper gene but maintains the encoded amino acid sequence. Techniques to shuffle sequences are known in the art. For example, a max scramble algorithm may be used as described in Coleman et al, Science 2008; 320: 1784-1787 and Mueller et al, Nat Biotechnol 2010; 28: 723-726, the disclosures of which are hereby incorporated by reference in their entirety. Briefly, the algorithm can involve stimulated annealing and bipartite matching to optimize the number of nucleotide changes and minimalize homology in the helper gene while using the same set of codons. Alternatively, an algorithm can involve minimalizing homology using the same set of codons but with the aim of achieving a more optimal codon pair bias score. Based on the experimentally determined codon usage for a certain species, there are expected frequencies with which distinct codon pairs should occur in a coding sequence. If codon pairs in a gene are overrepresented compared to the expected frequency, the codon pair bias score will be positive. Underrepresented codon pairs will have a negative score. In certain embodiments, the codon pair bias score is positive. For example, the codon pair bias score may be greater than about +/−5, greater than about +/−6, greater than about +/−7, greater than about +/−8, greater than about +/−9, greater than about +/−10, greater than about +/−11, greater than about +/−12, greater than about +/−13, greater than about +/−14, greater than about +/−15, greater than about +/−16, greater than about +/−17, greater than about +/−18, greater than about +/−19, greater than about +/−20, greater than about +/−21, greater than about +/−22, greater than about +/−23, greater than about +/−24, greater than about +/−25, greater than about +/−30, greater than about +/−35, greater than about +/−40, greater than about +/−45, greater than about +/−50, greater than about +/−55, greater than about +/−60, greater than about +/−65, greater than about +/−70, greater than about +/−75, greater than about +/−80, greater than about +/−85, greater than about +/−90, greater than about +/−95, or greater than about +/−100.

The aforementioned algorithms may be used to enhance or reduce helper gene expression. In certain embodiments, codon shuffling may be used to increase expression of the helper gene. Increased helper gene expression may facilitate enhanced complementation and virion production. In other embodiments, codon shuffling may be used to decrease expression of the helper gene. Expression of the codon shuffled helper gene may be increased or decreased by greater than about 1.2-fold relative to the same helper gene that is not codon shuffled. For example, expression of the codon shuffled helper gene may be increased or decrease by greater than about 1.5 fold, by greater than about 2 fold, by greater than about 2.5 fold, by greater than about 3 fold, by greater than about 3.5 fold, by greater than about 4 fold, by greater than about 4.5 fold, by greater than about 5 fold, by greater than about 5.5 fold, by greater than about 6 fold, by greater than about 7 fold, by greater than about 8 fold, by greater than about 9 fold, by greater than about 10 fold, by greater than about 20 fold, by greater than about 30 fold, by greater than about 40 fold, by greater than about 50 fold, or by greater than about 100 fold relative to the same helper gene that is not codon shuffled.

A helper gene may have no more than about 8 nucleotides in a row without a mutation relative to the wild-type gene. For example, a helper gene may have no more than about 5, about 6, about 7, about 8, about 9, about 10, about 11, about 12, about 13, about 14, or about 15 nucleotides in a row without a mutation relative to the wild-type gene. Additionally, a helper gene may have at least about 25% non-homology relative to the wild-type gene. For example, a helper gene may have at least about 25%, at least about 30%, at least about 35%, at least about 40%, at least about 45%, at least about 50%, at least about 55%, at least about 60%, at least about 65%, at least about 70%, at least about 75%, or at least about 80%, non-homology relative to the wild-type gene. Further, a helper gene may have at least about 25% non-homology relative to the wild-type gene. For example, a helper gene may have about 25%, about 30%, about 35%, about 40%, about 45%, about 50%, about 55%, about 60%, about 65%, about 70%, about 75%, or about 80%, non-homology relative to the wild-type gene. In a specific embodiment, a helper gene may have about 30% to about 35% non-homology relative to the wild-type gene.

In other embodiments, a first portion of a helper gene can be codon shuffled and a second portion of a helper gene can be wild-type. For example, a first portion may be about 100, about 150, about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1550, about 1600, about 1650, about 1700, or about 1750 nucleotides of the helper gene. Alternatively, a first portion may be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the total nucleotide sequence of the helper gene. In a specific embodiment, the helper gene comprises a sequence selected from the group consisting of SEQ ID NO:2, SEQ ID NO:3, SEQ ID NO:4, SEQ ID NO:5 and SEQ ID NO:6. In another specific embodiment, the helper gene consists of a sequence selected from the group consisting of SEQ ID NO:2, SEQ ID NO:3, SEQ ID NO:4, SEQ ID NO:5 and SEQ ID NO:6.

In particular, a codon shuffled helper gene is stably expressed in a cell line. The cell line is then infected with a replication incompetent virus. The cell line stably expressing the helper gene supplies the replication incompetent virus with gene products required for production of progeny virions and/or for production of infectious virions. In contrast, cell lines not expressing a helper gene do not result in production of progeny virions and/or infection virions upon infection with a replication incompetent virus. Further, cell lines expressing a helper gene that is not codon shuffled result in the production of wild-type revertant viruses that are replication competent without the need for the helper gene. Accordingly, the use of a codon shuffled helper gene prevents viral reversion.

In another aspect, a method of culturing a virus to prevent or reduce viral reversion as described herein can be used to produce a viral stock composition. In general, the method comprises stably expressing a codon shuffled helper gene in a host cell; culturing the host cell under conditions conducive to the propagation of a replication incompetent virus; and collecting the replicated virus. Methods of collecting replicated virus are known in the art. For example, viral supernatants comprising replicated virus can be collected one or more days following culture. The viral supernatants comprising replicated virus can be collected 1, 2, 3, 4, 5, 6, 7, 8, 9, 10, 11, 12, 13 or 14 days following culture. The method can further comprise additional passages of the replicated virus to increase numbers for viral stocks.

In still another aspect, the disclosure provides a vaccine composition formed from the viral stock produced via the method of culturing a virus as described herein. In general, the method comprises stably expressing a codon shuffled helper gene in a host cell; culturing the host cell under conditions conducive to the propagation of a replication incompetent virus; collecting the replicated virus; and forming the vaccine composition using the replicated virus. Vaccine compositions are described in greater detail below.

In still another aspect, the disclosure provides a composition comprising a gene therapy viral vector formed from the method of culturing a virus as described herein. In general, the method comprises stably expressing a codon shuffled helper gene in a host cell; culturing the host cell under conditions conducive to the propagation of a replication incompetent virus, wherein the replication incompetent virus expresses one or more genes of interest; collecting the replicated virus; and forming the composition comprising a gene therapy viral vector. The one or more genes of interest is any gene that can be employed for gene therapy. For example, the gene of interest may be a protein or enzyme that is mutated or deficient in a specific disease. The composition comprising a gene therapy viral vector can be formulated as a vaccine composition. Vaccine compositions are described in greater detail below.

(a) Adjuvants

The vaccine compositions of the disclosure may include a pharmaceutically acceptable excipient such as a suitable adjuvant. Suitable adjuvants include an aluminium salt such as aluminium hydroxide or aluminium phosphate, but may also be a salt of calcium, iron or zinc, or may be an insoluble suspension of acylated tyrosine, or acylated sugars, or may be cationically or anionically derivatised saccharides, polyphosphazenes, biodegradable microspheres, monophosphoryl lipid A (MPL), lipid A derivatives (e.g. of reduced toxicity), 3-O-deacylated MPL [3D-MPL], quit A, Saponin, QS21, Freund's Incomplete Adjuvant (Difco Laboratories, Detroit, Mich.), Merck Adjuvant 65 (Merck and Company, Inc., Rahway, N.J.), AS-2 (Smith-Kline Beecham, Philadelphia, Pa.), CpG oligonucleotides, bioadhesives and mucoadhesives, microparticles, liposomes, polyoxyethylene ether formulations, polyoxyethylene ester formulations, muramyl peptides or imidazoquinolone compounds (e.g. imiquamod and its homologues). Human immunomodulators suitable for use as adjuvants in the disclosure include cytokines such as interleukins (e.g. IL-1, IL-2, IL-4, IL-5, IL-6, IL-7, IL-12, etc), macrophage colony stimulating factor (M-CSF), tumour necrosis factor (TNF), granulocyte, macrophage colony stimulating factor (GM-CSF) may also be used as adjuvants.

(b) Non-Immunological Components of Vaccines

Vaccines of the disclosure will typically, in addition to the viral and adjuvant components mentioned above, comprise one or more "pharmaceutically acceptable carriers or excipients", which include any excipient that does not itself induce the production of antibodies harmful to the individual receiving the composition. Suitable excipients are typically large, slowly metabolized macromolecules such as proteins, saccharides, polylactic acids, polyglycolic acids, polymeric amino acids, amino acid copolymers, sucrose (Paoletti et al., 2001, Vaccine, 19:2118), trehalose (WO 00/56365), lactose and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate buffered physiologic saline is a typical carrier. A thorough discussion of pharmaceutically acceptable excipients is available in reference Gennaro, 2000, Remington: The Science and Practice of Pharmacy, 20$^{th}$ edition, ISBN: 0683306472.

Compositions of the disclosure may be lyophilized or in aqueous form, i.e. solutions or suspensions. Liquid formulations of this type allow the compositions to be administered direct from their packaged form, without the need for reconstitution in an aqueous medium, and are thus ideal for injection. Compositions may be presented in vials, or they may be presented in ready filled syringes. The syringes may be supplied with or without needles. A syringe will include a single dose of the composition, whereas a vial may include a single dose or multiple doses (e.g. 2 doses).

Liquid vaccines of the disclosure are also suitable for reconstituting other vaccines from a lyophilized form. Where a vaccine is to be used for such extemporaneous reconstitution, the disclosure provides a kit, which may comprise two vials, or may comprise one ready-filled syringe and one vial, with the contents of the syringe being used to reconstitute the contents of the vial prior to injection.

Vaccines of the disclosure may be packaged in unit dose form or in multiple dose form (e.g. 2 doses). For multiple dose forms, vials are preferred to pre-filled syringes. Effective dosage volumes can be routinely established, but a typical human dose of the composition for injection has a volume of 0.5 mL.

In one embodiment, vaccines of the disclosure have a pH of between 6.0 and 8.0, in another embodiment, vaccines of the disclosure have a pH of between 6.3 and 6.9, e.g. 6.6±0.2. Vaccines may be buffered at this pH. Stable pH may be maintained by the use of a buffer. If a composition comprises an aluminium hydroxide salt, a histidine buffer may be used (WO03/009869). The composition should be sterile and/or pyrogen free.

Compositions of the disclosure may be isotonic with respect to humans.

Vaccines of the disclosure may include an antimicrobial, particularly when packaged in a multiple dose format. Antimicrobials may be used, such as 2-phenoxyethanol or parabens (methyl, ethyl, propyl parabens). Any preservative is preferably present at low levels. Preservative may be added exogenously and/or may be a component of the bulk antigens which are mixed to form the composition (e.g. present as a preservative in pertussis antigens).

Vaccines of the disclosure may comprise detergent e.g. a Tween (polysorbate), such as Tween 80. Detergents are generally present at low levels e.g. <0.01%.

Vaccines of the disclosure may include sodium salts (e.g. sodium chloride) to give tonicity. The composition may comprise sodium chloride. In one embodiment, the concentration of sodium chloride in the composition of the disclosure is in the range of 0.1 to 100 mg/mL (e.g. 1-50 mg/mL, 2-20 mg/mL, 5-15 mg/mL) and in a further embodiment the concentration of sodium chloride is 10±2 mg/mL NaCl e.g. about 9 mg/m L.

Vaccines of the disclosure will generally include a buffer. A phosphate or histidine buffer is typical.

Vaccines of the disclosure may include free phosphate ions in solution (e.g. by the use of a phosphate buffer) in order to favour non-adsorption of antigens. The concentration of free phosphate ions in the composition of the disclosure is in one embodiment between 0.1 and 10.0 mM, or in another embodiment between 1 and 5 mM, or in a further embodiment about 2.5 mM.

(c) Vaccine Formulations

The vaccine composition of the disclosure may be in a pharmaceutical composition comprising nanoparticles being composed of macromolecules and linear polyethylenimine (l-PEI) or l-PEI derivative, and a pharmaceutically acceptable solvent. This composition may be administered orally, topically, inhaled, or may be administered via other suitable means. For instance, see Toke et al. Inter J of Pharmaceutics 392(2010) 261-7; Lorincz et al., Nanomedicine: Nanotechnology, Biology, and Medicine 8 (2012) 497-506; and Toke et al., Gene Therapy (2014), 1-9, each of which are hereby incorporated by reference in their entirety.

The amount of virus in each vaccine dose is selected as an amount which induces an immunoprotective response without significant, adverse side effects in typical vaccines. Such amount will vary depending on which specific viruses are employed. An optimal amount for a particular vaccine can be ascertained by studies involving observation of antibody titres and other responses in subjects.

The vaccine composition can be formulated into various dosage forms and administered by a number of different means that will deliver a therapeutically effective amount of the virus. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980). In a specific embodiment, a composition may be a topical formulation.

II. Method of Use

In other aspects, the disclosure provides a method of treating a viral infection in a subject. The method comprises administering an effective amount of a vaccine composition of the disclosure to the subject. The term "infection" as used herein includes presence of virus in or on a subject, which, if its replication were inhibited, would result in a benefit to the subject. The term "treat", "treating" or "treatment" as used herein refers to administering a composition of the disclosure for prophylactic and/or therapeutic purposes. The term "prophylactic treatment" refers to treating a subject who is not yet infected, but who is susceptible to, or otherwise at a risk of infection. The term "therapeutic treatment" refers to administering treatment to a subject already suffering from infection. The term "treat", "treating" or "treatment" as used herein also refers to administering a composition of the disclosure in order to: (i) reduce or eliminate either a viral infection or one or more symptoms of the viral infection, or (ii) retard the progression of a viral infection or of one or more symptoms of the viral infection, or (iii) reduce the severity of a viral infection or of one or more symptoms of the viral infection, or (iv) suppress the clinical manifestation of a viral infection, or (v) suppress the manifestation of adverse symptoms of the viral infection.

In still other aspects, the disclosure provides a method of administering gene therapy to a subject. The method comprises administering an effective amount of a composition comprising a gene therapy viral vector of the disclosure to the subject. Additionally, the disclosure provides a method of treating a tumor in a subject. The method comprises administering an effective amount of a composition comprising an oncolytic virus of the disclosure to the subject.

A subject may be a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include poultry, pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In certain embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc.

The term "effective amount" as used herein refers to an amount, which has a therapeutic effect or is the amount required to produce a therapeutic effect in a subject. For example, a therapeutically or pharmaceutically effective amount of a composition of the disclosure is the amount of replication incompetent virus required to produce a desired therapeutic effect as may be judged by clinical trial results, model animal infection studies, and/or in vitro studies (e.g. cell lines). The effective or pharmaceutically effective amount depends on several factors, including but not limited to, the virus involved, characteristics of the subject (for example height, weight, sex, age and medical history), severity of infection, and the composition used. For prophylactic treatments, a therapeutically or prophylactically effective amount is that amount which would be effective to prevent an infection.

Administration may be accomplished by parenteral injection (intramuscularly, intraperitoneally, intradermally, subcutaneously, intravenously, or to the interstitial space of a tissue); or by rectal, oral, vaginal, topical, transdermal, intranasal, ocular, aural, pulmonary or other mucosal administration. In one embodiment, administration is by intramuscular injection to the thigh or the upper arm. Injection may be via a needle (e.g. a hypodermic needle, electroporation device), but needle free injection may alternatively be used. A typical intramuscular dose is 0.5 mL. In another embodiment, administration is by topical administration. Vaccine preparations adapted for topical administration may be formulated as ointments, creams, suspensions, lotions, powders, solutions, pastes, gels, sprays, aerosols, oils, or salves. Topical administration may also involve the use of transdermal administration such as transdermal patches, a DermaPrep device or iontophoresis devices. In still another embodiment, administration is by oral administration. Formulations for the various methods of administration are described above.

Viruses affect various areas of the body and so the compositions of the disclosure may be prepared in various forms. For example, the compositions may be prepared as injectables, either as liquid solutions or suspensions. The compositions may preferably be prepared for oral or topical administration as liquid or lyophilized liposome formulations as described above. The composition may be prepared for pulmonary administration e.g. as an inhaler, using a fine powder or spray. The composition may be prepared as a suppository or pessary. The composition may be prepared for nasal, aural or ocular administration e.g. as spray, drops, gel or powder (see e.g. Almeida & Alpar, 1996, J Drug Targeting, 3:455; Bergquist et al., 1998, APMIS, 106:800).

Following initial administration of the vaccine composition, subjects may receive one or several additional administrations of the vaccine composition adequately spaced. Dosing treatment can be a single dose schedule or a multiple dose schedule. Suitable timing between doses (e.g. between 4-16 weeks) can be routinely determined. In certain embodiments, a vaccine composition of the disclosure may be administered as multiple doses. Administration may be daily, weekly, twice weekly, monthly, twice monthly, every 6 weeks, every 3 months, every 6 months or yearly. For example, administration may be every 5 weeks, every 6 weeks, every 7 weeks or every 8 weeks. Alternatively, administration may be every 2 months, every 3 months, every 4 months, every 5 months, or every 6 months. The duration of treatment can and will vary depending on the subject and the infection to be treated. For example, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, administration may be every 4 weeks for 6 months to a year and then administration may be every year thereafter.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Preventing Wild-Type Reversion Through Codon Shuffling During Complementation in Trans of Replication-Defective Viruses The propensity for DNA viruses such as herpesviruses to undergo homologous recombination has been harnessed for decades in the generation of recombinant viruses. However, the recombinogenic nature of the viral genome poses a major problem in efforts to generate replication-defective viruses and potential vaccine strains. Defining evolutionary pressures that select for codon organization within a particular viral or host gene is an active area of investigation (10). From these studies, it is clear that manipulating the codon distribution in specific viral genes leads to changes in protein levels that impact viral replication and fitness (5-7, 11). Codon shuffling is a gene-design methodology whereby codon usage frequency is preserved for a given coding sequence, but synonymous codons are shuffled like a deck of cards using computer-assisted algorithms (5-7). Importantly, this type of synthetic manipulation to alter codon distribution in a viral gene effectively changes the nucleotide sequence in a gene of interest without altering the amino acid sequence. In addition, the genetic deck can be manipulated to enhance codon-pair bias or any number of variables to potentially increase or decrease protein levels. We therefore sought to repurpose the codon-shuffling algorithm to design synthetic complementation constructs in which regions of nucleotide homology to a viral genome are minimized to prevent recombination, yet factors that favor protein production of the complementing construct are maintained or enhanced.

As a test system for determining whether codon shuffling provides an effective method for complementing mutant herpesvirus, we chose murine gammaherpesvirus 68 (MHV68)—a well characterized rodent gammaherpesvirus that is genetically and phenotypically related to human pathogens Epstein-Barr virus and Kaposi sarcoma-associated herpesvirus (3, 12, 13). The replication and transcription activator protein, RTA, is an immediate-early viral gene product that is absolutely essential for the initiation of the lytic replication gene-expression cascade (9). The essential role for RTA was demonstrated using a recombinant virus that contained a translation stop codon and frameshift mutation (ORF50.stop, RTA-null MHV68) at aa 116 in RTA protein (9). Stocks of the RTA-null virus can only be produced in cells engineered to express wild-type RTA protein (9). Given the propensity of herpesviruses to undergo homologous recombination, the necessity for RTA in replication and thus strong positive selection pressure for revertant wild-type viruses, it is not surprising that wild-type reversion occurs frequently during the generation of RTA-null virus stocks in complementing cell lines (1 wild-type revertant in $1\times10^5$-$3\times10^4$ PFU, (9)). Hence, RTA-null virus provides an ideal and stringent test of the utility of the codon-shuffling approach for complementation.

We designed five unique codon-shuffled (CS) RTA complementation constructs, designated CS-RTA1-5. Alignments of CS-RTA constructs to WT-RTA encoding nucleotide sequence are shown in FIG. 1. Effects of codon-shuffling on codon-pair bias (CPB), CpG content and percent identity to wild-type sequence are provided in Table 1. To briefly summarize, the CS-RTA constructs were designed using the codon-shuffling algorithm as detailed in the Methods for the Examples (5). All synthetic RTA constructs maintain the same frequency of codon usage as WT-RTA (referred to as the codon adaptation index, Table 1). CS-RTA1 and CS-RTA2 have the most nucleotide changes across the entire open reading frame (ORF), but have very different CPB scores. CPB has differential impacts on translation efficiency such that the degree of a positive or negative score often correlates with increased and decreased levels of protein expression respectively (10). CS-RTA2 was designed with a search algorithm to minimalize homology using the same set of codons, but with the aim of achieving a more optimal CPB score than CS-RTA1, which was designed with the goal of maximizing nucleotide changes. Since the mutation that generates a stop codon in the ORF50.stop RTA-null MHV68 mutant is in the 5' region of the ORF, we reasoned that reversion-associated homologous recombination might be limited to the genomic region directly 5' and 3' to the stop mutation. Thus we designed three constructs that limited sequence changes to the first 388 nt of RTA. CS-RTA3 is a fusion of the first 381 nt of CS-RTA1 with the remainder of the WT-RTA sequence that had 136 nt changes and a negative CPB score. CS-RTA4 was designed with parameters to restore a more optimal CPB score, and was only applied to the first 381 nt of ORF50, resulting in 109 nt changes. CS-RTA5 is a fusion of the first 384 nt of CS-RTA2 with the remainder of the WT-RTA sequence, leading to 133 nt changes and a corresponding optimal CPB.

Figure 2B:
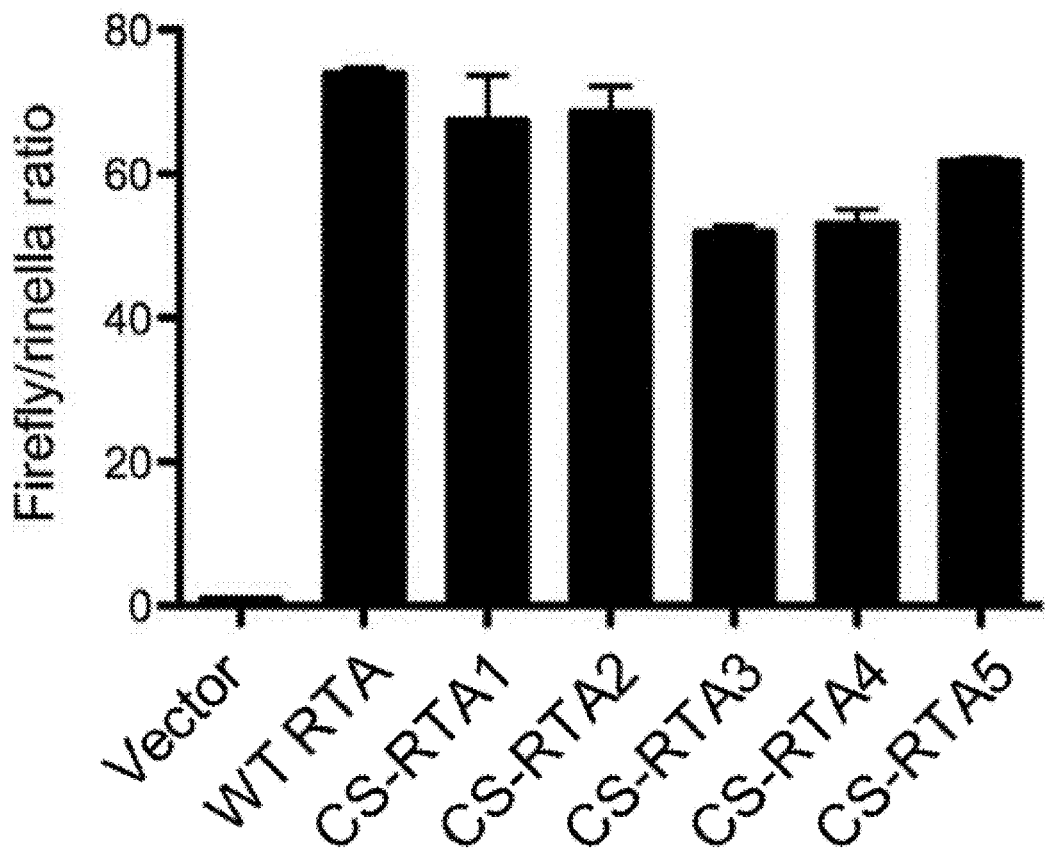
Figure 2C:
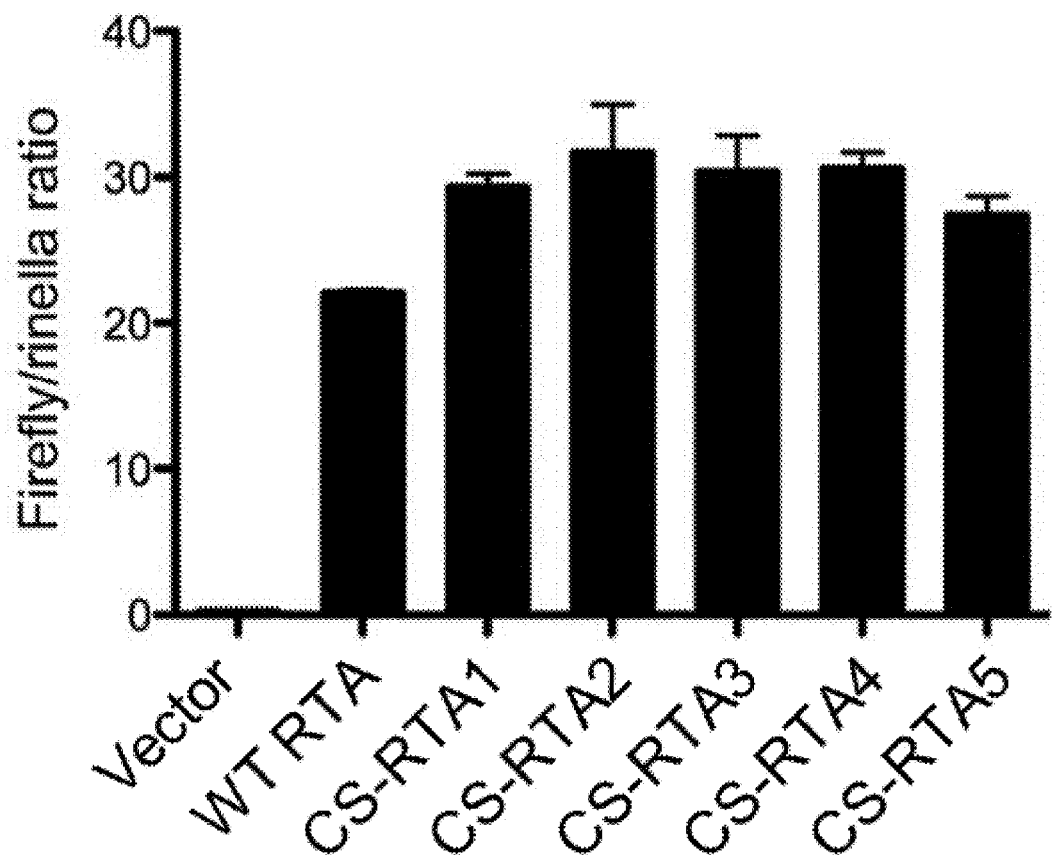
Figure 3A:
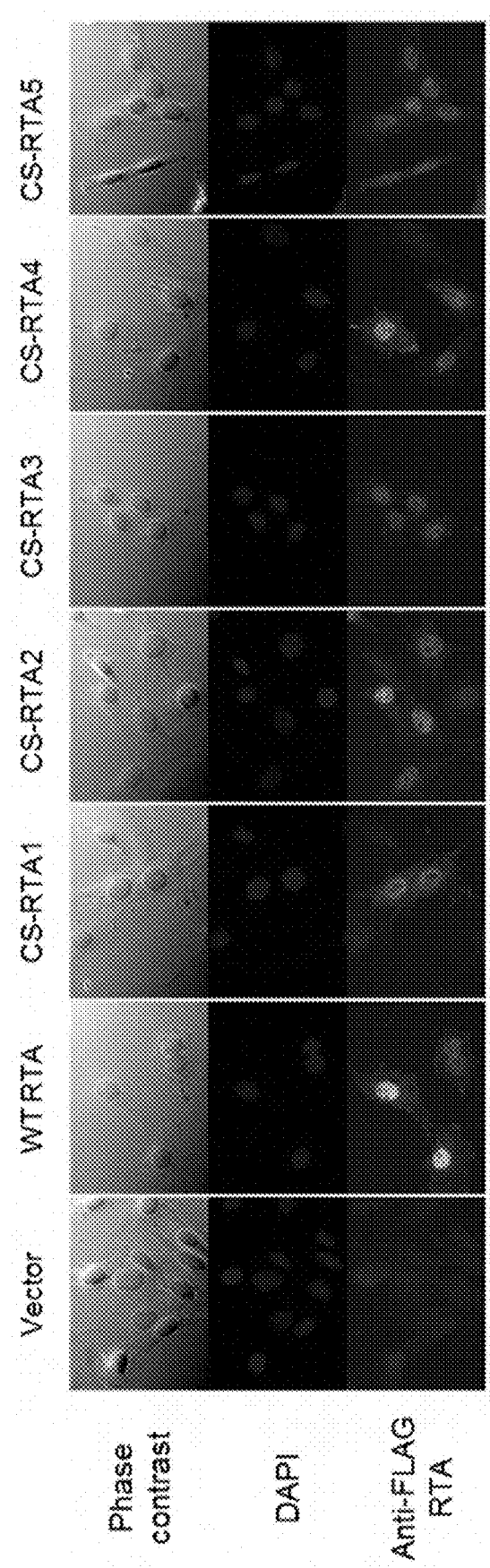
FIG. 3A and FIG. 3B depicts images and an immunoblot showing CS-RTA constructs express and localize to the nucleus in stable cell lines. MSCV-based retroviruses were produced in a packaging cell line, and NIH 3T12 fibroblasts were transduced with retroviruses encoding each of the indicated constructs.
Figure 3B:
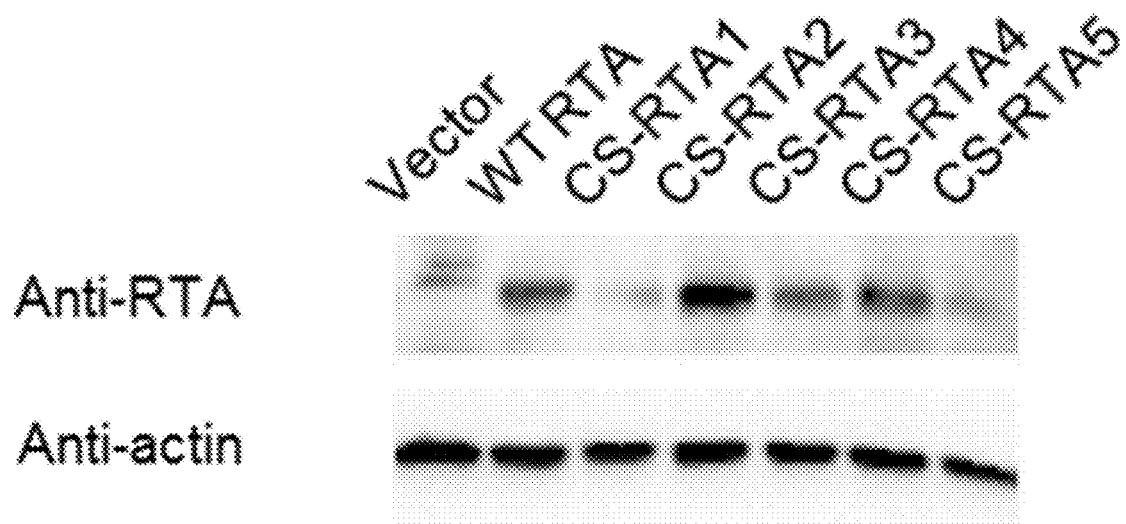

To evaluate the capacity of CS-RTA constructs to complement infection by RTA-null MHV68, we generated stable NIH 3T12 fibroblast lines by transduction with retroviruses encoding WT-RTA, CS-RTA1-5, or empty vector control. Because manipulating CPB can alter the translation efficiency of proteins (10), we first sought to confirm that CS-RTA constructs were translated and functional. CS-RTA constructs were detectable in immunoblot analyses performed following transient transfection of 293T cells (FIG. 2A), indicating that CS-RTA constructs were translation competent. Since RTA is a viral transcription factor, we next performed luciferase reporter assays in transiently-transfected cells to functionally test whether CS-RTA constructs were capable of activating promoters for RTA-responsive viral genes ORF57 and ORF72 (2, 8). CS-RTA constructs and WT-RTA all potently induced ORF57 and ORF72 promoters (FIG. 2B, FIG. 2C). Together, these data demonstrate that CS-RTA constructs are efficiently translated and fully functional. Finally, indirect immunofluorescence and immunoblot analyses confirmed that WT-RTA and CS-RTA proteins were expressed and localized to the nucleus in stable cell lines generated for complementation studies (FIG. 3A, FIG. 3B).

Figure 4A:
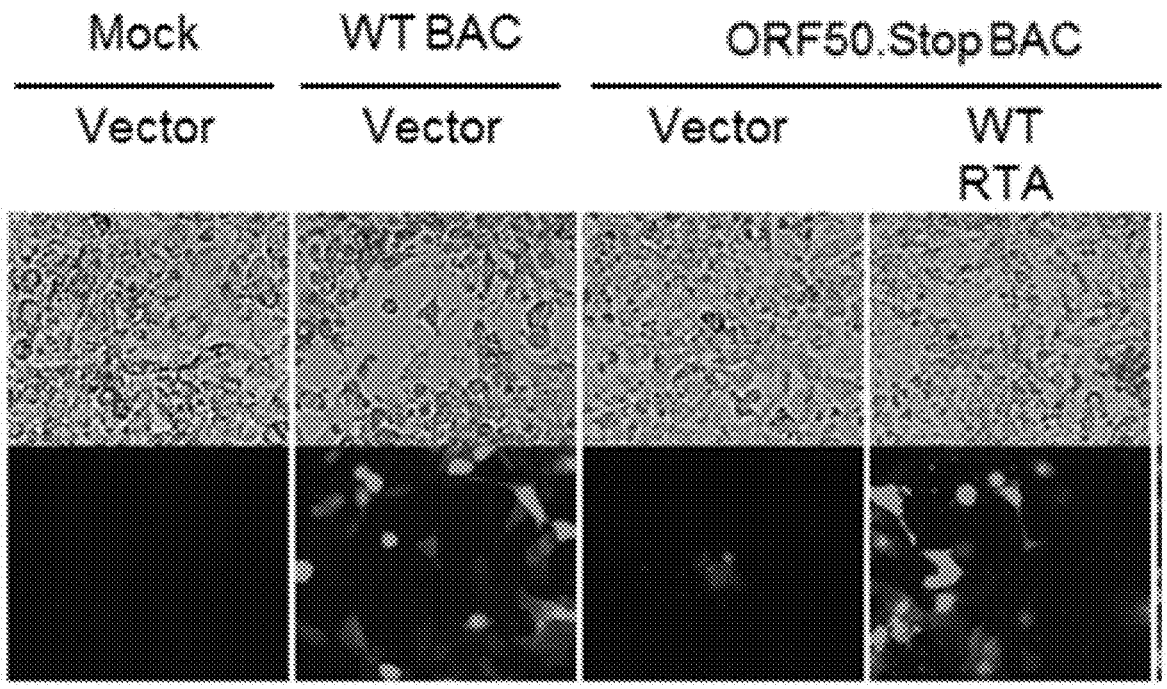
FIG. 4 depicts images showing that CS-RTAs complement RTA-deficient MHV68 in stable 3T12 cell lines. Vector control or WT-RTA or CS-RTA stable cell lines were transfected as indicated with either WT-MHV68 BAC or ORF50.stop MHV68 BAC. Phase contrast and epifluorescence microscopy to detect virus-encoded GFP were performed 8 days post-transfection to visualize cytopathic effect and viral spread within cultures.
Figure 4B:
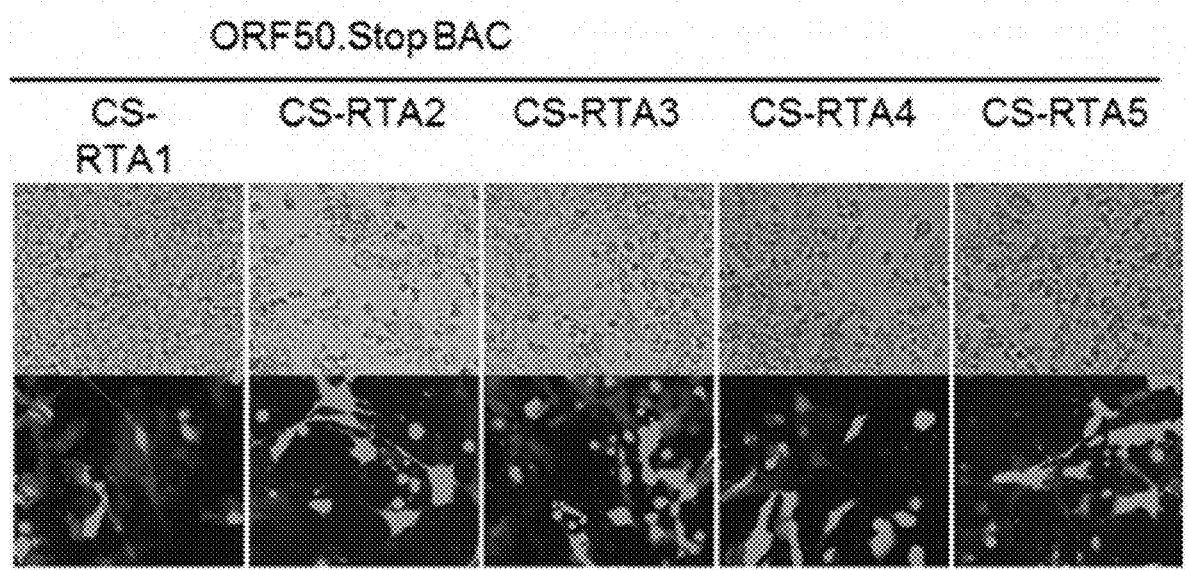

To evaluate the capacity of CS-RTA constructs to support viral replication, vector control, WT-RTA or CS-RTA-expressing cells were transfected with RTA-null ORF50.Stop MHV68 BAC (9), and cells were observed over time for evidence of viral replication. As a positive control, vector control cells also were transfected with WT-MHV68 BAC. Three days post-transfection, green fluorescent protein (GFP, expressed from the MHV68 BAC vector) was readily detectable in scattered individual cells, indicating that the cells were successfully transfected with the MHV68 BAC. In wild-type and CS-RTA-expressing cells, GFP fluorescence became stronger and spread over time to neighboring cells in a manner resembling transfections with WT-MHV68 BAC DNA (FIG. 4). In contrast, GFP fluorescence remained dim and restricted to isolated cells in vector control cells transfected with ORF50.Stop MHV68 DNA (FIG. 4). Thus, complementation by CS-RTA constructs, like WT-RTA, enables propagation and cell-to-cell spread of RTA-null MHV68.

Figure 5A:
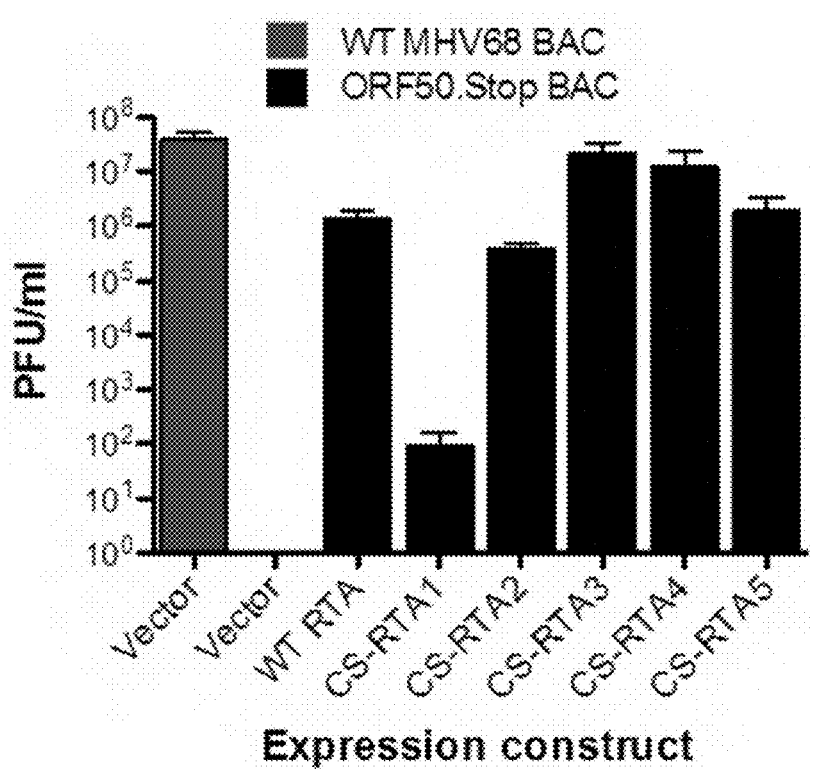
FIG. 5A, FIG. 5B and FIG. 5C depict graphs and images showing CS-RTAs support efficient production of RTA-null MHV68.
Figure 5B:
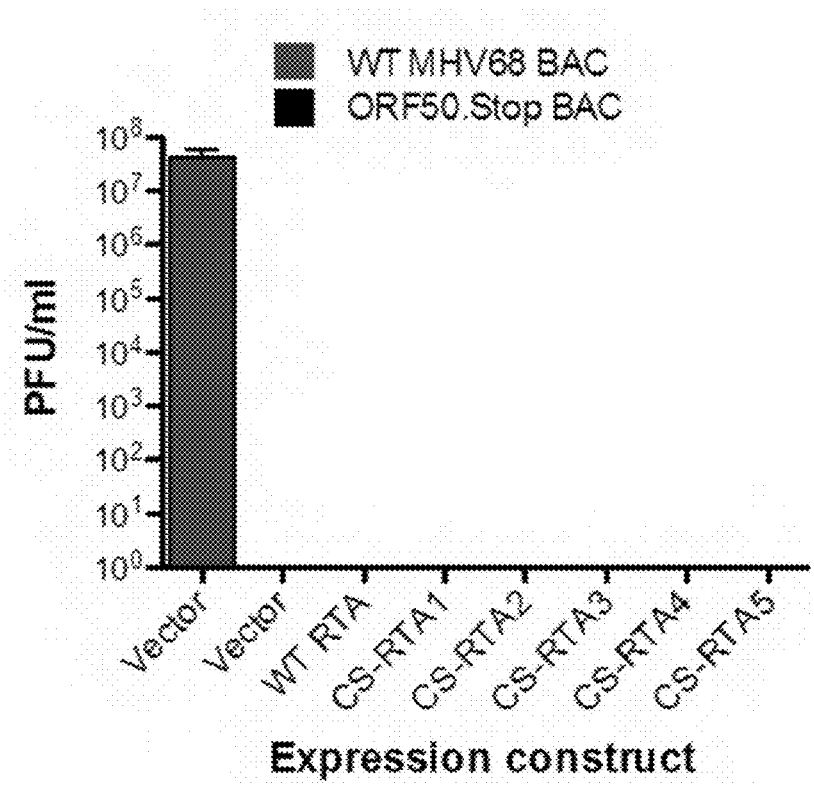
Figure 5C:
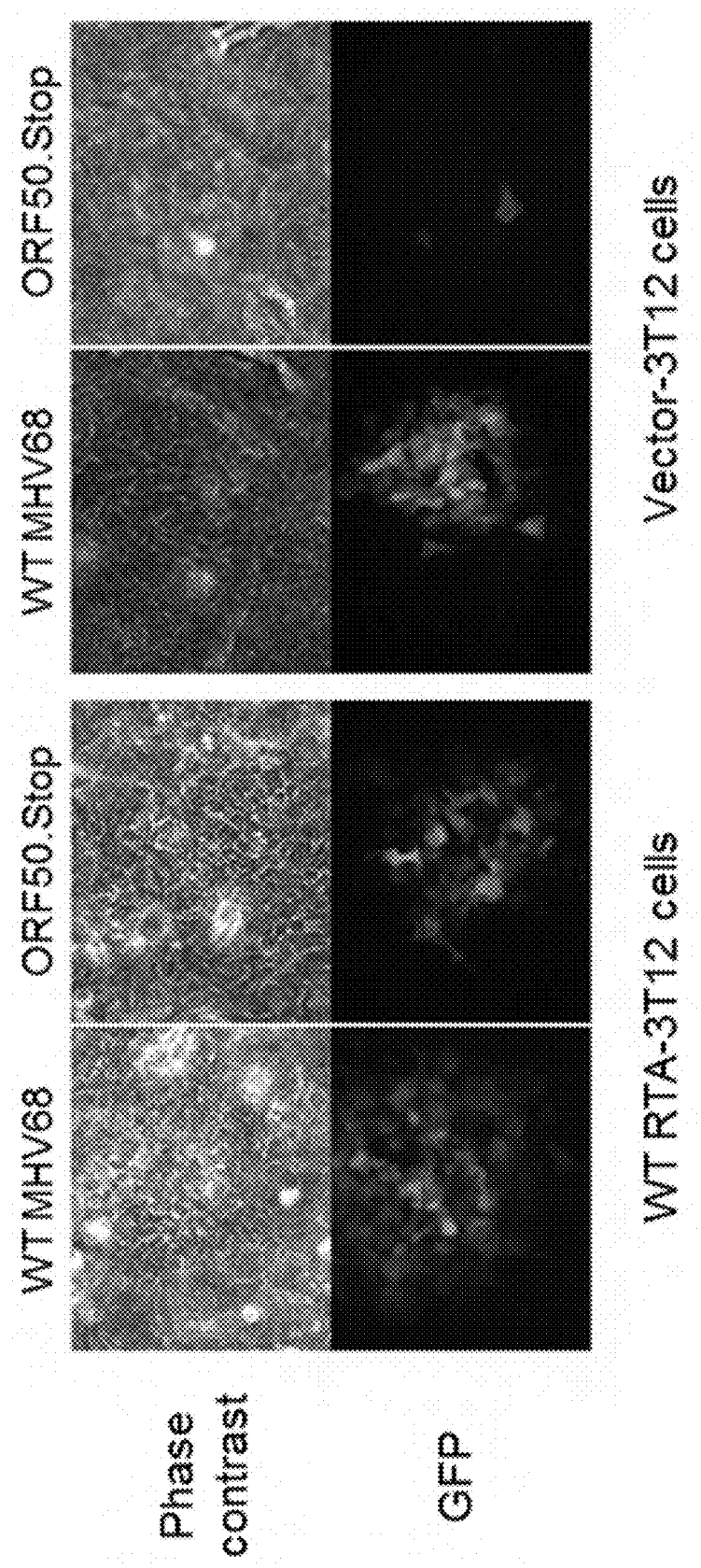

Culture supernatants were collected from transfected cells and propagated for two additional passages on their cognate cell line to generate working virus stocks, which were titrated by plaque assay on WT-RTA-expressing 3T12 fibroblasts. RTA-null virus stocks derived from vector control cells yielded no detectable plaques, while titers of $10^5$ to $10^7$ PFU per ml were quantified for WT-RTA and 4 of 5 CS-RTA stable cell lines (FIG. 5A). Interestingly, CS-RTA1 was much less efficient than other CS-RTA constructs, yielding titers of approximately 100 PFU per ml. CS-RTA1 had the most nucleotide changes and the lowest CPB score of all codon-shuffle constructs, suggesting that factors beyond simple amino acid sequence impact the capacity for complementation. Plaques were not detected for any RTA-null MHV68 stocks titrated in parallel on vector control cells (FIG. 5B), though GFP+ cells indicative of infection were present when infected cells were examined by fluorescence microscopy (FIG. 5C). These data demonstrate that CS-RTA constructs complement RTA-null MHV68 replication, and the majority of constructs rescued viral replication approximately as efficiently as WT-RTA.

Figure 6A:
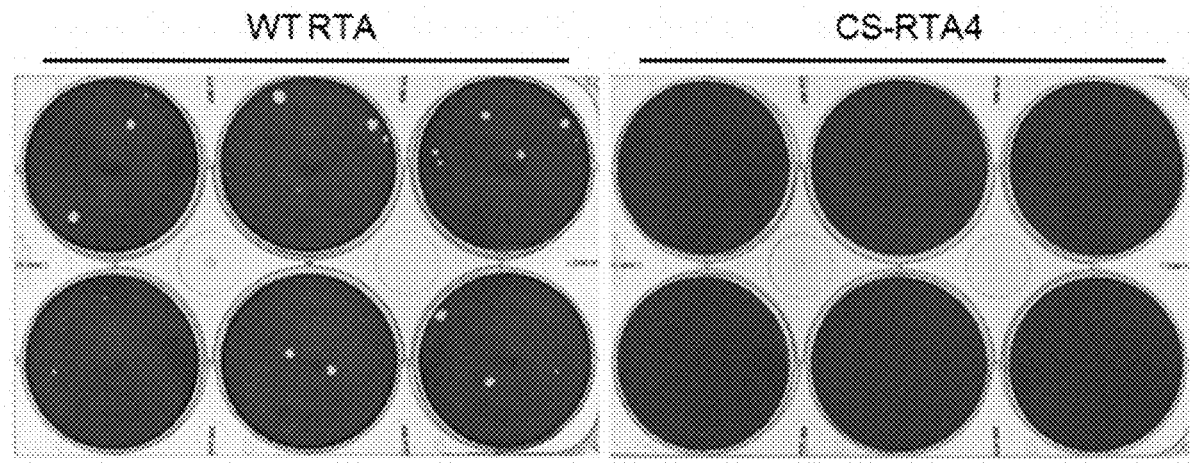
Figure 6B:
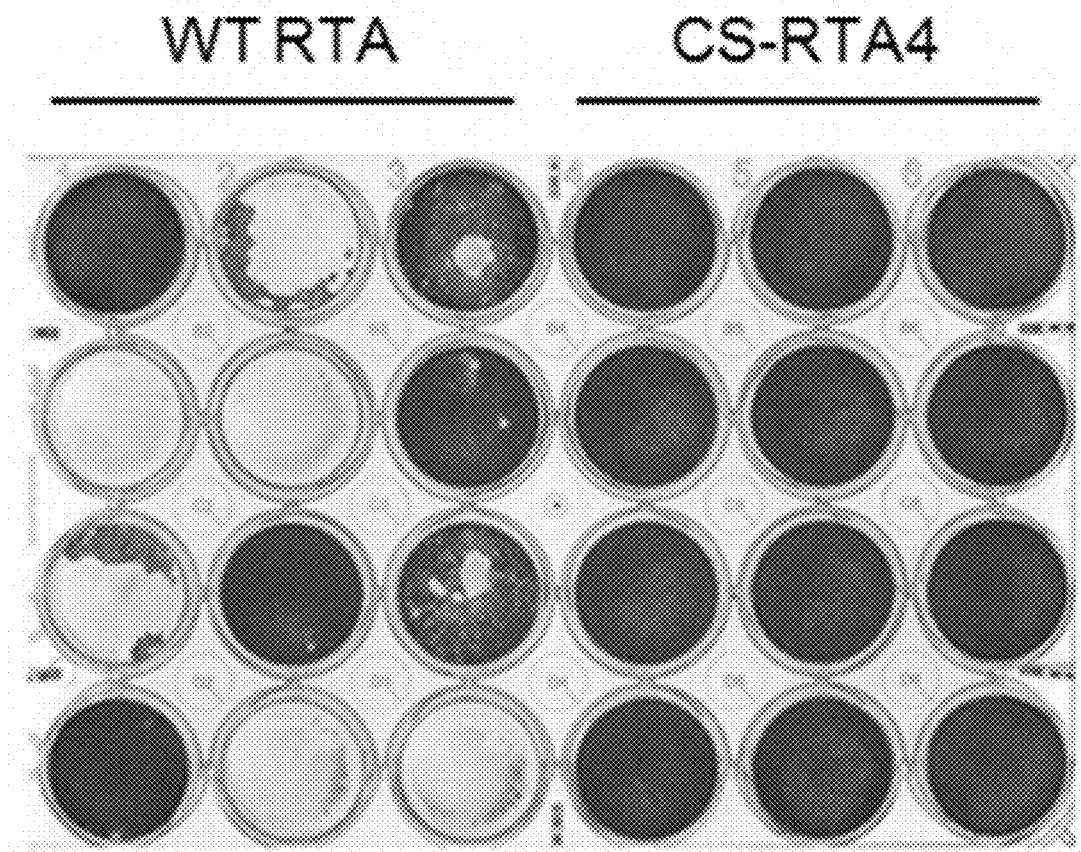
Figure 6C:
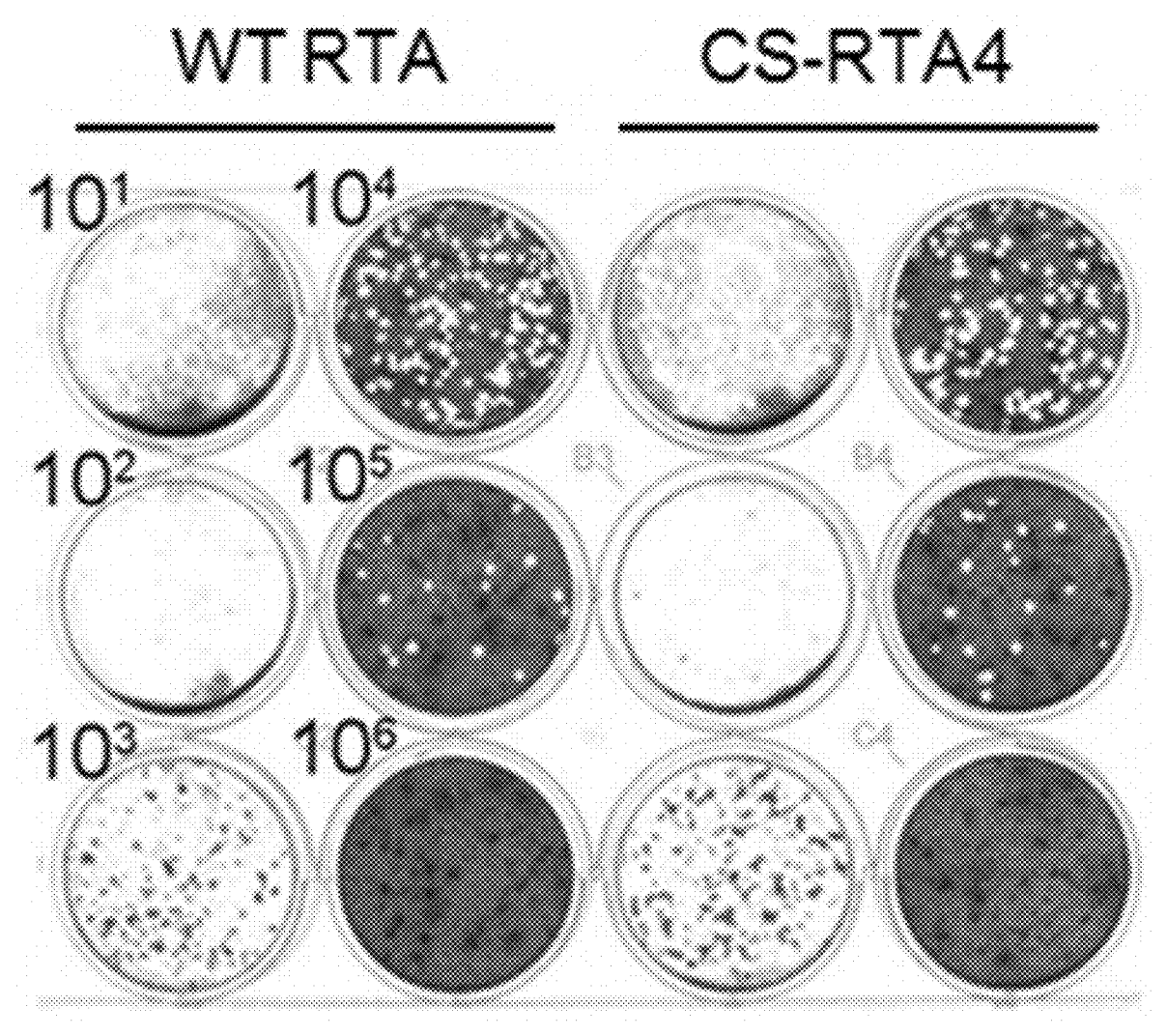

To determine whether complementation of RTA-null MHV68 using CS-RTA expressing cells reduced the risk of wild-type reversion in comparison to mutant virus produced in cells expressing WT-RTA. For these experiments, we concentrated virus stocks by centrifugation to ca. $1 \times 10^8$ PFU per ml in order to increase the sensitivity of detecting revertant wild-type viruses produced during complementation. To detect revertant wild-type viruses we performed plaque assays for each concentrated RTA-null stock on vector control 3T12 cell lines. While virus produced on WT-RTA expressing cells yielded plaques on control cells (reversion frequency in initial experiments of 1.0 PFU per $10^8$ complemented PFU), no wild-type reversion was detected in any stock derived from cells stably expressing CS-RTA constructs, although titers were comparable on WT-RTA-expressing cells. It is worth noting that reversion frequencies in our experiments were much lower than previously reported (9). We speculate that this is due to the use of retroviral transduction, rather than the traditional plasmid-based approaches used before, as the means to generate complementing cell lines. As a re-test, we repeated the complementation experiment with WT-RTA and CS-RTA4, the construct which contains the fewest number of nucleotide changes (109 nt, Table 1) from wild-type coding sequence, all present in the first 384 nucleotides of the CS construct. Again, only WT-RTA-complemented viruses formed plaques on vector control 3T12 cells (FIG. 6A, reversion frequency of 1.12 PFU per $10^6$ complemented PFU), although each virus stock had comparable titers on WT-RTA-3T12 cells (FIG. 6C). As a more sensitive test, we also performed cytopathic effect assays (CPE) to detect virus reversion. The MHV68 CPE assay is ca. 10-fold more sensitive than plaque assays for revealing the presence of replication-competent MHV68 (17). Virus stocks produced in WT-RTA-expressing 3T12s induced CPE in 8 of 12 wells of control 3T12s, while stocks derived from RTA-CS4 cells did not yield CPE in any wells (FIG. 6B). Together, these data strongly suggest that codon shuffling has the capacity to limit wild-type reversion during complementation of mutant viruses.

To test the reproducibility of the finding that employing CS RTA for complementation prevents reversion, we performed ten additional independent complementation trials with WT-RTA and CS-RTA4 stable 3T12 cells (Table 2, repeats 2 to 11). Of the eleven virus stocks produced by complementation with WT-RTA, eight exhibited reversion at a level of detection of ca. 1 PFU in $10^8$ PFU, with reversion frequencies ranging from 0.12-11.98 per $10^6$ complemented PFU. In contrast, no revertant wild-type viruses were detected in any of the eleven virus stocks produced in CS-RTA4 stable cells. These results demonstrate that codon-shuffling designed synthetic vectors for complementation effectively eliminated the risk of wild-type reversion when producing high-titer stocks of a replication defective herpesvirus.

Figure 7:
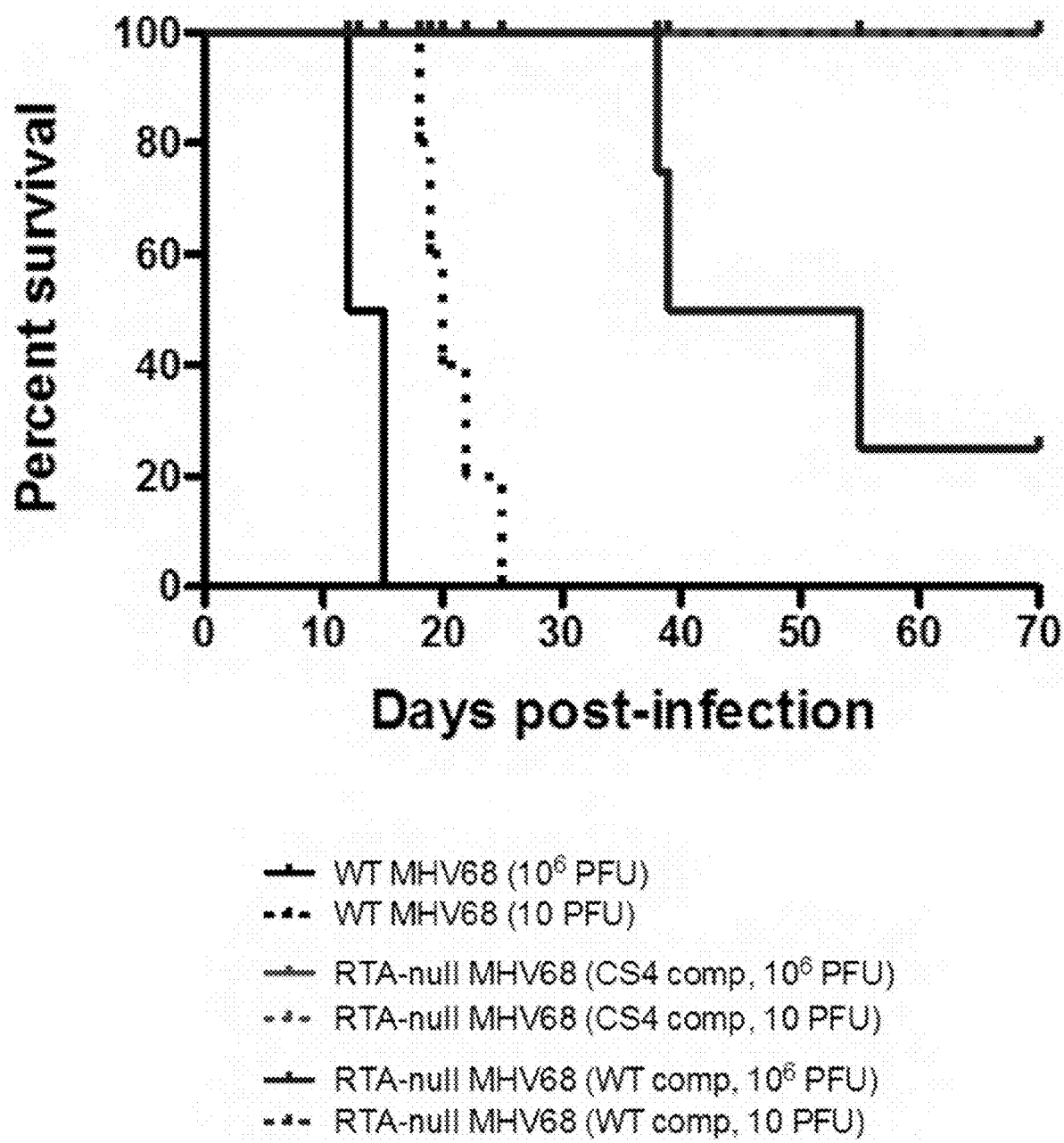
FIG. 7 depicts a graph showing RTA-null MHV68 produced in CS-RTA4 complementing cells does not kill immune compromised mice. Severe combined immune deficient (SCID) mice were inoculated with either high-dose ($10^6$ PFU) or low-dose (10 PFU) of either WT-MHV68, RTA-null MHV68 produced on WT-RTA stable cells (WT comp) with a reversion frequency of ca. 1 in $10^6$ PFU, or RTA-null MHV68 produced on CS-RTA4 stable cells (CS4 comp) with no detectable revertants. Mortality was monitored over time after infection.
Figure 8A:
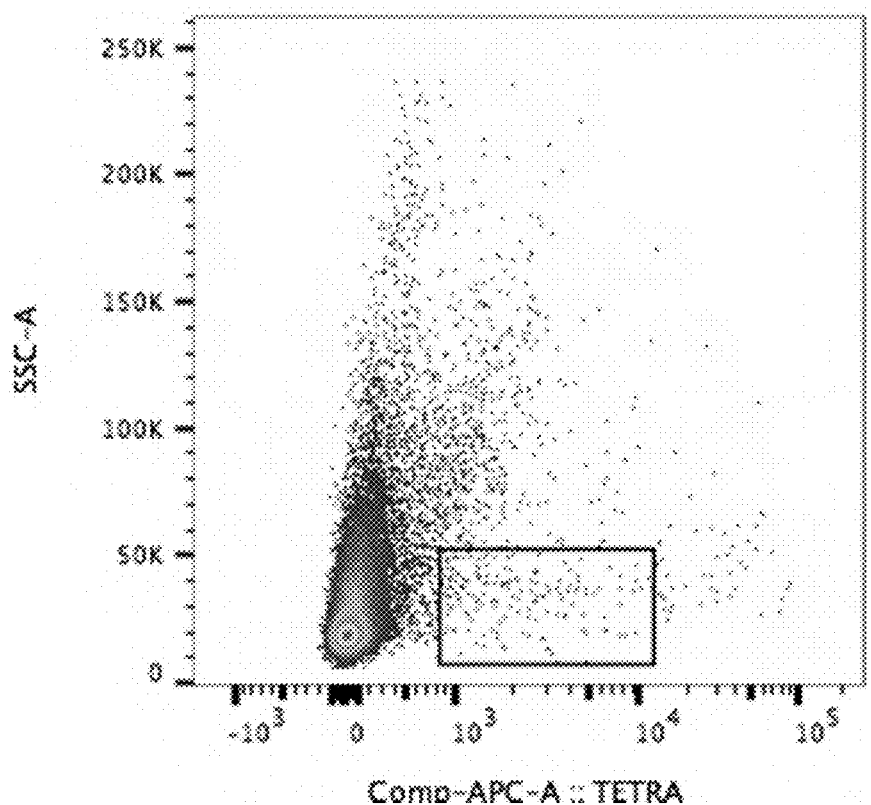
FIG. 8 depicts CD8+ T cell response in non-infected, RTA-null ORF50.STOP infected and wild type infected C57BL/6 mice. C57BL/6 mice were mock infected or infected intraperitoneally with $10^6$ PFU of either WT-MHV68 or RTA-null ORF50.STOP MHV68 that was produced in codon-shuffling based producer cell line CS-RTA4. Cells were stained with antibodies to detect cytotoxic T cell marker CD8, activation marker CD69, and MHC class I tetramers (FIG. 8A-D p56 or FIG. 8E-H p79) that present MHV68 epitopes. Labeled cells were analyzed by flow cytometry.
Figure 8B:
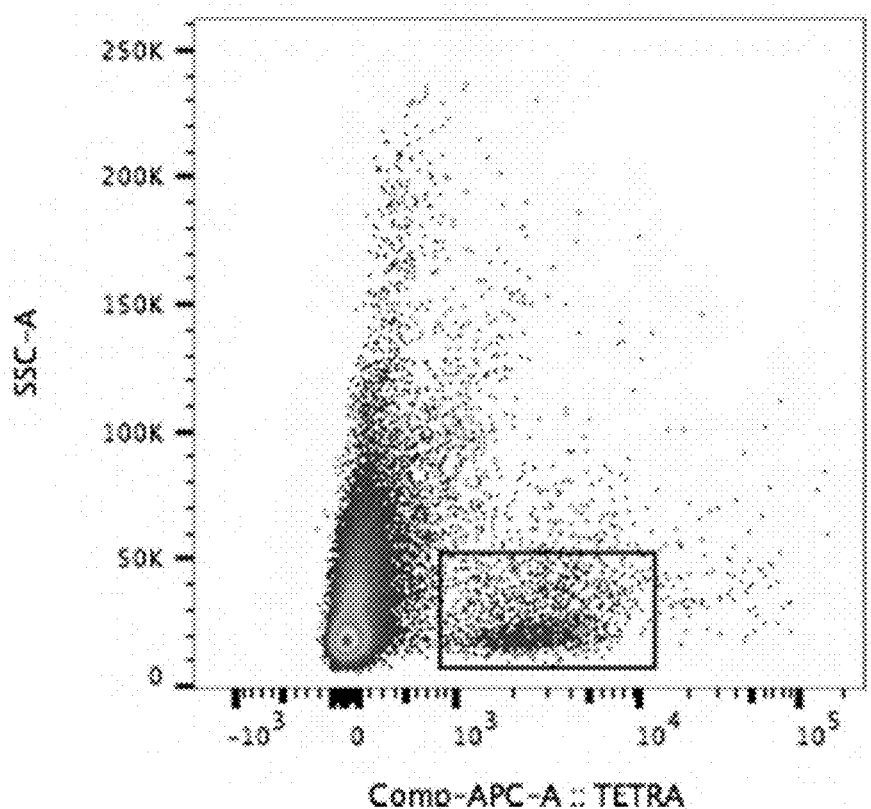
Figure 8C:
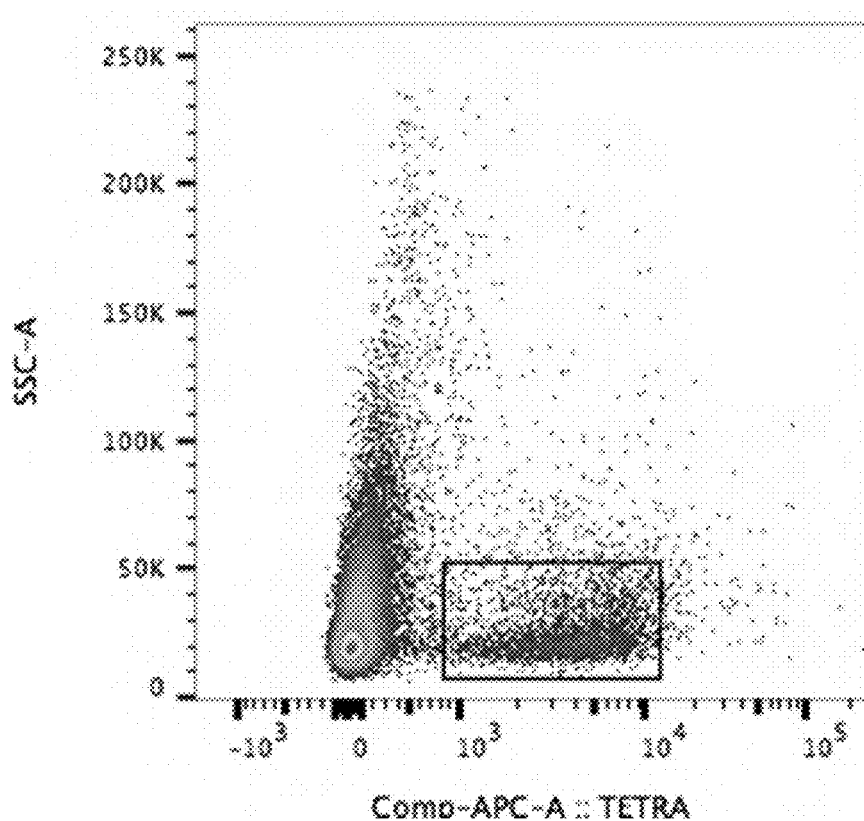
Figure 8D:
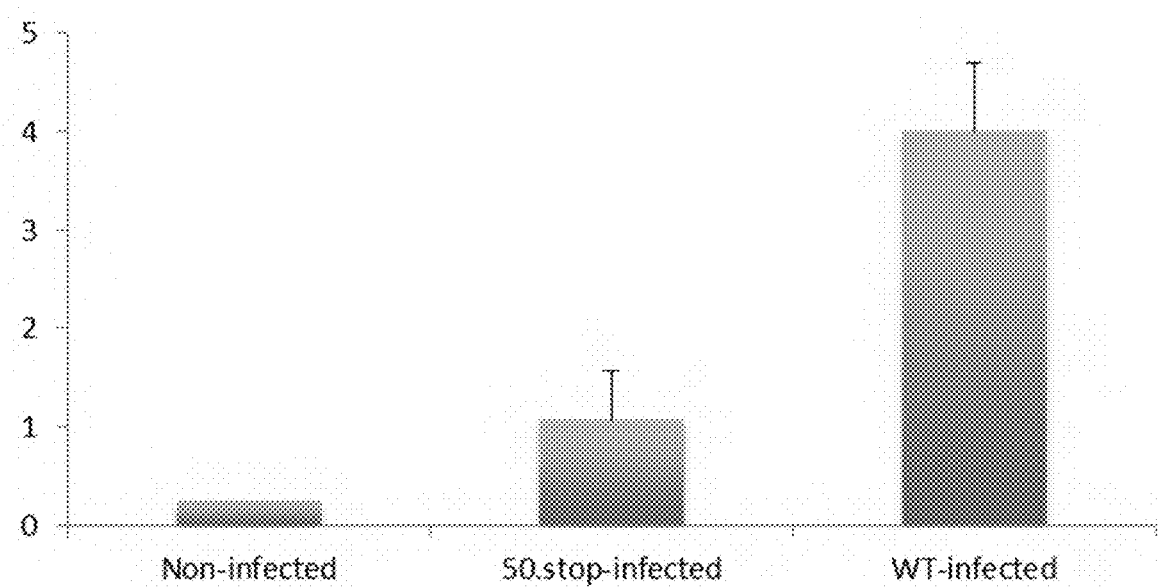
Figure 8E:
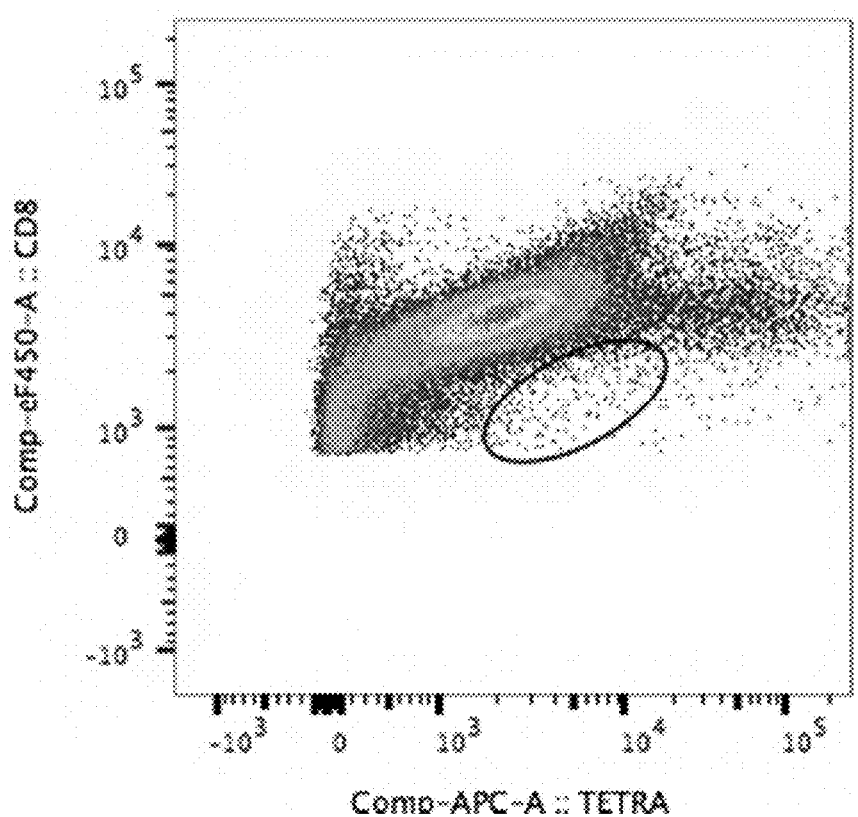
Figure 8F:
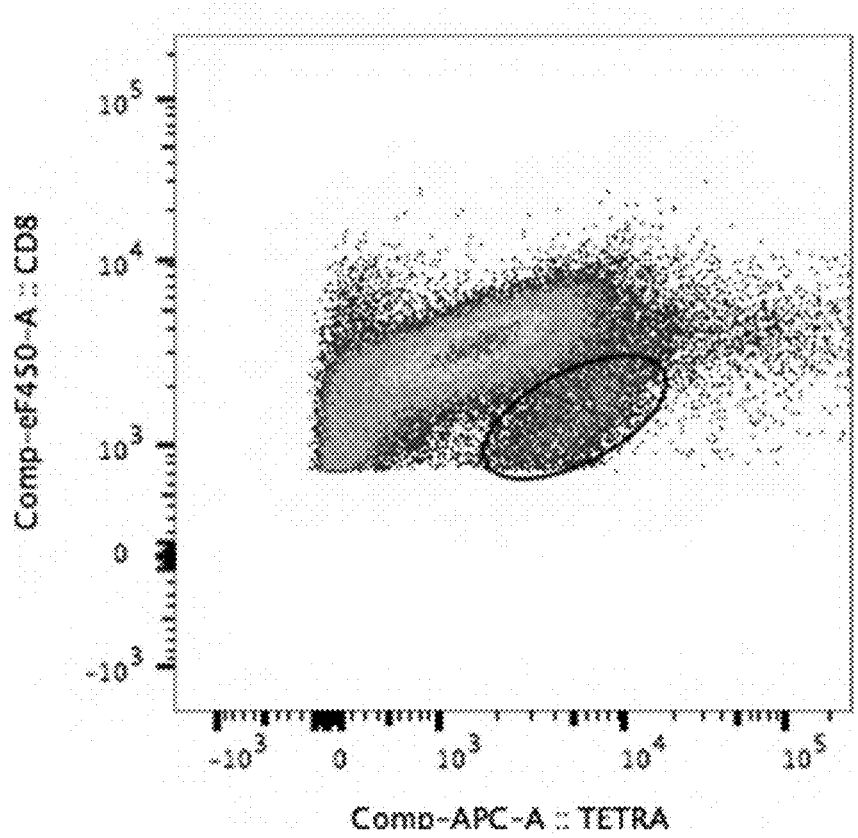
Figure 8G:
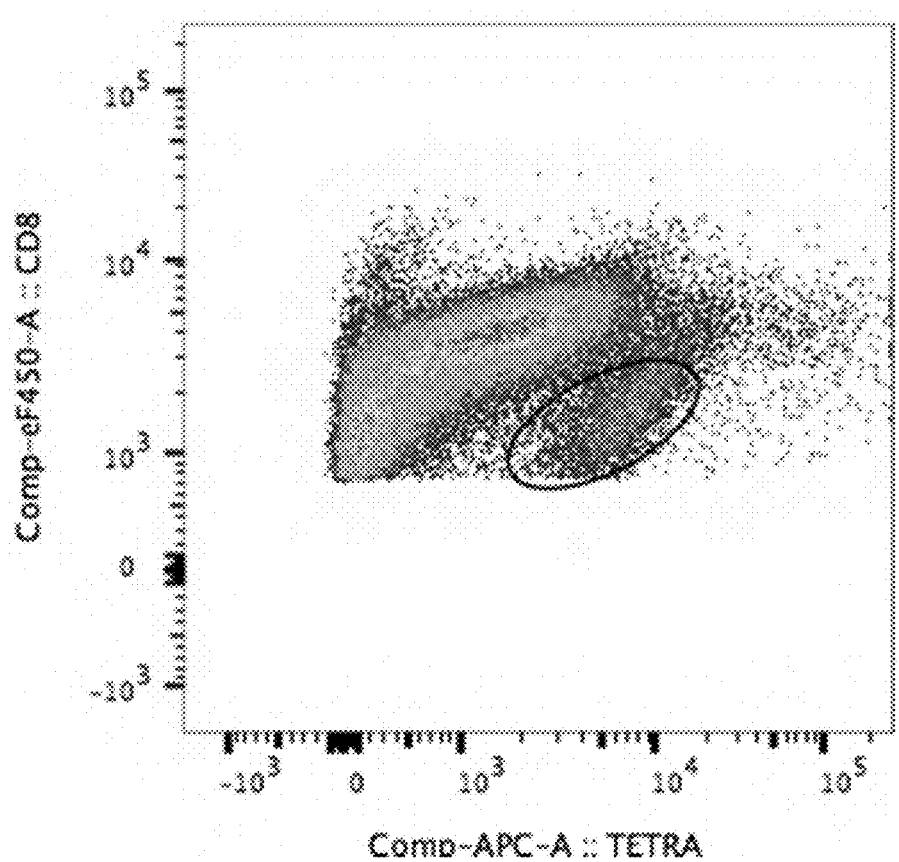
Figure 8H:
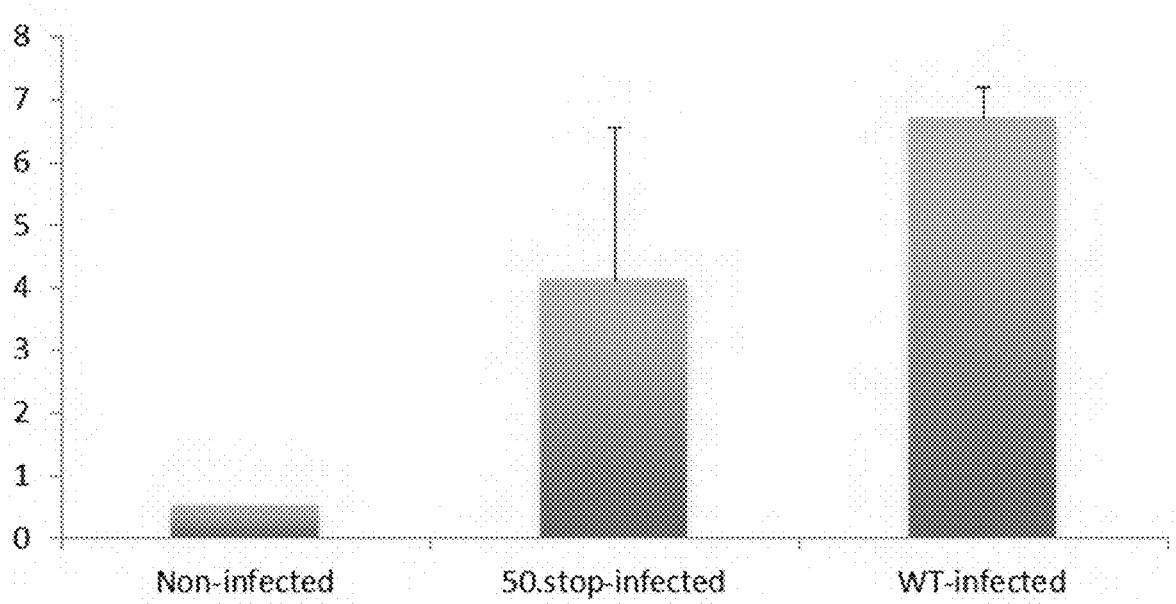
Figure 9:
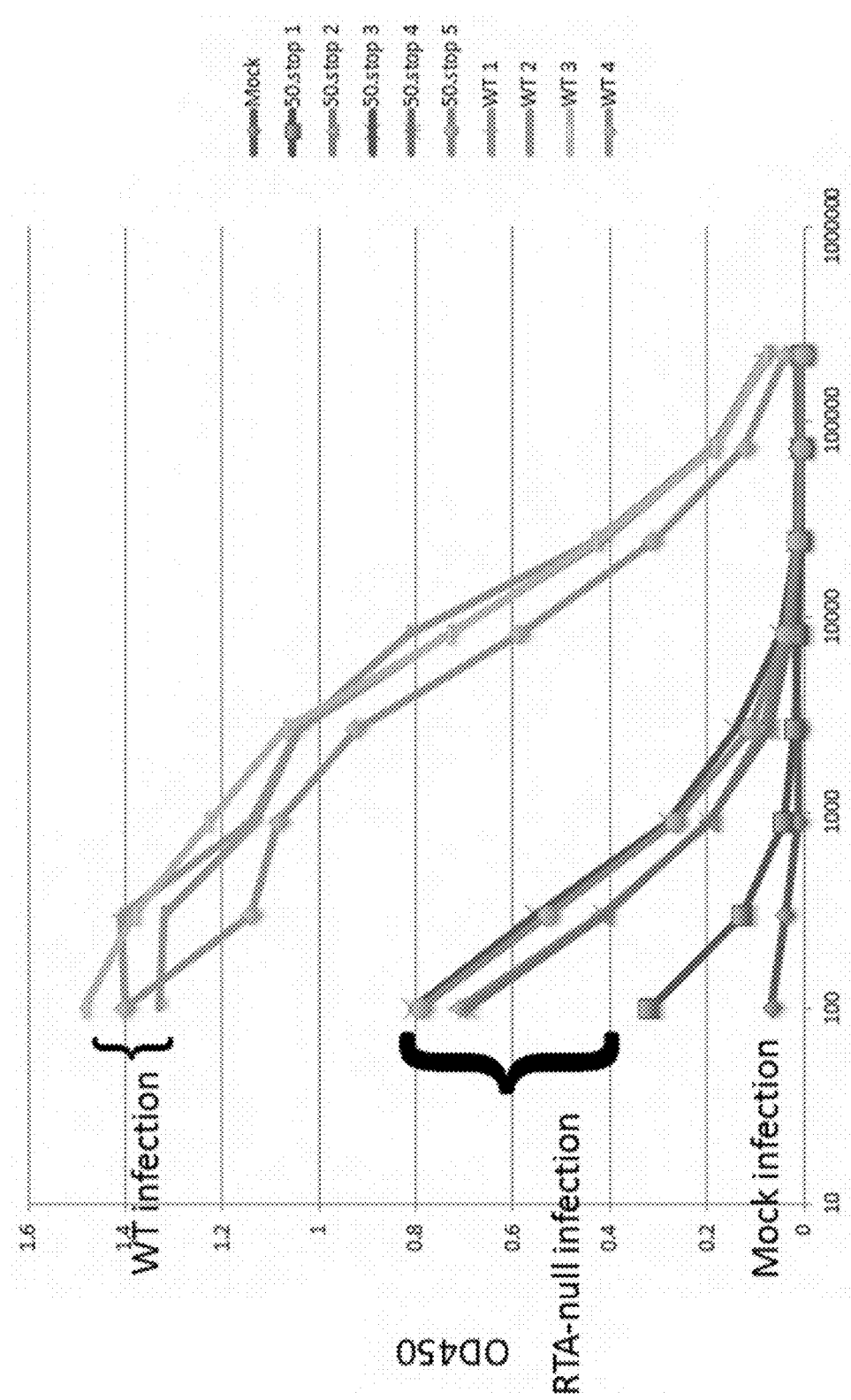
FIG. 9 graphically depicts virus specific antibody response. C57BL/6 mice were mock infected or infected intraperitoneally with $10^6$ PFU of either WT-MHV68 or RTA-null ORF50.STOP MHV68 that was produced in a codon-shuffling based producer cell line. Mice were sacrificed on day 42 post-inoculation, and sera were collected. Sera were evaluated in MHV68-specific ELISAs.

To confirm in vivo that RTA-null stocks derived from codon shuffling were devoid of replication competent MHV68 and simultaneously evaluate the safety of potential vaccine stocks generated using this method, we infected severe combined immunodeficient (SCID) mice with WT-RTA or CS-RTA4 complemented RTA-null virus. SCID mice are unable to generate adaptive immune responses and are particularly sensitive to infections that are not cleared by innate immune responses. Infection of SCID mice with WT-MHV68 causes lethality in 100% of infections (4, 15), thus we reasoned that the presence of WT-MHV68 in RTA-null stocks would result in mortality in SCID mice. Infections with either 10 PFU or $10^6$ PFU of WT-MHV68 served as positive controls for disease in these experiments. Mice infected with $10^6$ PFU of WT-MHV68 succumbed by 12-15 dpi, while those infected with 10 PFU succumbed between 18-25 dpi (FIG. 7). Infection with $10^6$ PFU of the RTA-null MHV68 derived from complementation in WT-RTA cells stock with a reversion rate of ca. 1 PFU in $10^6$ complemented PFU caused death in 3 of 5 animals between 38 and 55 dpi. This result illustrates the potential problem of traditional complementation approaches for producing vaccine stocks. However, no mortality occurred over a 70 day period for SCID mice infected with 10 PFU or $10^6$ PFU of RTA-null virus derived in CS-RTA4 cells. We conclude that application of this technology is suitable for generating high-titer, yet replication-defective virus stocks that are safe to use in immunocompromised hosts for studies of early infection events or host immune responses.

To test if a replication-dead virus, produced by codon-shuffling-mediated complementation, stimulates a virus-specific CD8+ T cell response C57BL/6 mice were mock infected or infected intraperitoneally with $10^6$ PFU of either wild-type MHV68 or RTA-null ORF50.STOP MHV68 that was produced in codon-shuffling based producer cell line CS-RTA4. Mice were sacrificed on day 16 post-inoculation, and spleen cells were isolated. Cells were stained with antibodies to detect cytotoxic T cell marker CD8, activation marker CD69, and MHC class I tetramers (p56 or p79; FIG. 8) that present MHV68 epitopes. Labeled cells were analyzed by flow cytometry. The data demonstrate that vaccination with a single dose of replication-dead virus produced using the codon-shuffling-based complementation method is capable of stimulating a virus-specific cytotoxic T cell response.

The ability to generate a virus-specific antibody response was examined to further test the immune response produced by a replication-dead virus produced by codon-shuffling-mediated complementation. C57BL/6 mice were mock infected or infected intraperitoneally with $10^6$ PFU of either wild-type MHV68 or RTA-null ORF50.STOP MHV68 that was produced in codon-shuffling based producer cell line CS-RTA4. Mice were sacrificed on day 42 post-inoculation, and sera were collected. Sera were evaluated in MHV68-specific ELISAs. The data demonstrate that a replication-dead virus produced using the codon-shuffling-based complementation method is capable of stimulating a virus-specific antibody response.

Methods for the Examples.

Design of Codon-Shuffled RTA Sequences.

Codon bias is a phenomenon that different organisms exhibit preferred codon usage distributions, which have been shown to influence the speed of translation (Gardin et al. (2014). Measurement of average decoding rates of the 61 sense codons in vivo. *Elife*, 3, e03735). In contrast, codon-pair bias describes the frequency of paired codon occurrence relative to expectation under an independence assumption, factoring in codon bias. If codon pairs in a gene are overrepresented compared to the expected frequency, the codon pair score will be positive. Underrepresented codon pairs will have a negative score. The codon usage of each RTA-encoding ORF50 construct was determined relative to the codon usage table for *Mus musculus*. The relative adaptation of each codon was used to calculate the codon adaptation index for the entire gene. Codon-pair bias scores were calculated based on the codon-pair bias scoring human reference table since codon pair bias is highly conserved among mammals.

CS-RTA1 was designed using the max scramble algorithm previously described (5, 6). Briefly, the algorithm employs stimulated annealing and bipartite matching to simultaneously optimize the number of nucleotide changes and minimalize homology in ORF50 while using the same set of codons. CS-RTA2 was designed using a search algorithm to minimize homology with the same set of codons but with the aim of achieving a more optimal codon pair bias score. CS-RTA3 is a fusion of the first 381 nt of CS-RTA1 with the remainder of the WT-RTA sequence. CS-RTA4 was designed with a similar algorithm as for CS-RTA2, but with parameters to restore a more optimal codon pair bias score, and was only applied to the first 381 nt of ORF50. CS-RTA5 is a fusion of the first 384 nt of CS-RTA2 with the remainder of the WT-RTA sequence. Regions of homology less than 6 nucleotides were not counted against the score.

Unique CS-RTA sequences were synthesized by Blue Heron Biotechnology (now OriGene) with the addition of an N-terminal FLAG-tag and flanking BglII and XhoI restriction sites. An internal BglII site was mutated to facilitate cloning. The source of ORF50 encoding RTA, plasmid psg50 (9), was found to have two mutations compared to the published reference genome (U97553.2; (16)). The nonsynonymous C to T mutation at nucleotide 242 of ORF50 was repaired back to wild-type sequence. A second silent C to T mutation at nucleotide 1225 was left in the wild-type ORF50 sequence and was also present in CS-RTA3, CS-RTA4, and CS-RTA5. CS-RTA1 and CS-RTA2 were cloned into the BglII and XhoI sites of pMSCV-puro (Clontech). CS-RTA3, CS-RTA4, and CS-RTA5 were generated by splice-overlap extension PCR and cloned into BglII and XhoI sites of pMSCV-puro. Fidelity of cloning was verified by automated sequencing. Sequence alignments were performed using Geneious software.

Cells and Viruses.

NIH 3T12 fibroblasts and BOSC23 ecotropic retroviral packaging cells were purchased from ATCC. Cells were cultured in Dulbecco's modified Eagle medium (DMEM) supplemented with 10% fetal bovine serum, 2 mM L-glutamine, 100 units/ml penicillin, and 100 µg/ml streptomycin. Cells were cultured at 37° C. in atmosphere containing 5% $CO_2$. Murine stem cell virus (MSCV)-based retroviral vectors were produced by transfecting BOSC23 cells with empty pMSCV or individual pMSCV-RTA constructs using lipofectamine (Invitrogen) according to the manufacturer's instruction. Two days post-transfection, retroviral supernatants were harvested and filtered through 0.45 µm filters (Merck Millipore) to remove cell debris. Filtered retroviruses were added directly to NIH 3T12 fibroblasts in culture medium supplemented with 4 µg/ml polybrene. Transduced cells were selected by adding 5 µg/ml puromycin two days post-transduction and expanded in the presence of puromycin for two weeks until puromycin resistant cells were obtained.

Wild-type MHV68 (1) or ORF50.STOP (9) MHV68 BACs were transfected into either vector control cells or cell lines encoding either WT-RTA or CS-RTA1-5 using lipofectamine and plus reagents (Invitrogen). Viral supernatants were harvested from transfected cell lysates seven days post-transfection and passaged two additional times on the appropriate cognate cell line to produce working stocks for experimentation. All viral stocks were harvested by two freeze-thaw cycles followed by centrifugation at 500 g for 10 min at 4° C. to remove cell debris. Viral stocks were concentrated by centrifugation at 35,000 g for 90 min at 4° C. followed by resuspension of virion pellets in fresh medium of 1/10 original volume.

MHV68 Plaque Assay and Cytopathic Effect Assay.

Viruses were serially diluted and titrated by plaque assay as described previously (14) on vector control 3T12 cells to evaluate reversion for RTA-null viruses and WT-RTA 3T12 cells to determine titers of complemented RTA-null stocks. Wild-type reversion titrations were performed by plating undiluted virus directly onto vector control cells in plaque assays on 6-well plates. Cells were fixed with formalin and stained with crystal violet seven days post-infection for plaque visualization and enumeration. Cytopathic effect assays were performed by incubating 50 µl of concentrated virus stocks with vector control 3T12 cells in 24-well plates. Cells were fixed and stained with crystal violet in formalin ten days post-infection, and cytopathic effect was observed.

Mice and Infections.

CB.17 severe-combined immunodeficient (SCID) mice were purchased from Harlan laboratories (Envigo, Indianapolis, Ind.). All experiments were performed in accordance with a protocol approved by the Institutional Animal Care and Use Committee of Stony Brook University. 6 week old female CB.17 SCID mice were infected with 10 PFU or $10^6$ PFU of recombinant MHV68 in 0.5 ml cMEM by intraperitoneal injection.

TABLE 1

Parametric analyses of codon-shuffled constructs relative to wild-type RTA.

| Constructs | nt changes | Codon adaptation index | Codon-pair bias score | Codon-pair bias score per codon | CpG observed vs. expected ratio |
|---|---|---|---|---|---|
| WT-RTA | 0 | 0.7319 | 0.1846 | 0.0003 | 0.4524 |
| CS-RTA1 | 642 | 0.7321 | −67.6078 | −0.1160 | 0.7489 |
| CS-RTA2 | 614 | 0.7321 | 69.2674 | 0.1188 | 0.4411 |
| CS-RTA3 | 136 | 0.7316 | −24.1314 | −0.0414 | 0.5670 |
| CS-RTA4 | 109 | 0.7319 | −6.8171 | −0.0117 | 0.5244 |
| CS-RTA5 | 133 | 0.7207 | 12.2735 | 0.0211 | 0.5262 |

TABLE 2

Wild-type reversion in WT-RTA or CS-RTA4 complemented RTA-null ORF50.STOP virus stocks.

| Repeat number | Titer on WT-RTA-3T12 cells (PFU per ml) | Titer on pMSCV-3T12 cells (PFU per ml) | Reversion per million viruses |
|---|---|---|---|
| RTA-null MHV68 stocks produced in WT-RTA stable 3T12 cells | | | |
| 1 | 17 × 10⁶ | 19 | 1.12 |
| 2 | 54 × 10⁶ | 30 | 0.56 |
| 3 | 54 × 10⁶ | Not detected* | Not detected |
| 4 | 69 × 10⁶ | 8 | 0.12 |
| 5 | 60 × 10⁶ | 15 | 0.24 |
| 6 | 84 × 10⁶ | 690 | 8.21 |
| 7 | 42 × 10⁶ | Not detected | Not detected |
| 8 | 63 × 10⁶ | 15 | 0.24 |
| 9 | 42 × 10⁶ | 503 | 11.98 |
| 10 | 60 × 10⁶ | 38 | 0.63 |
| 11 | 39 × 10⁶ | Not detected | Not detected |
| RTA-null MHV68 stocks produced in CS-RTA4 stable 3T12 cells | | | |
| 1 | 20 × 10⁶ | Not detected | Not detected |
| 2 | 33 × 10⁶ | Not detected | Not detected |
| 3 | 30 × 10⁶ | Not detected | Not detected |

TABLE 2-continued

Wild-type reversion in WT-RTA or CS-RTA4 complemented RTA-null ORF50.STOP virus stocks.

| Repeat number | Titer on WT-RTA-3T12 cells (PFU per ml) | Titer on pMSCV-3T12 cells (PFU per ml) | Reversion per million viruses |
|---|---|---|---|
| 4 | 30 × 10$^6$ | Not detected | Not detected |
| 5 | 36 × 10$^6$ | Not detected | Not detected |
| 6 | 25 × 10$^6$ | Not detected | Not detected |
| 7 | 27 × 10$^6$ | Not detected | Not detected |
| 8 | 33 × 10$^6$ | Not detected | Not detected |
| 9 | 29 × 10$^6$ | Not detected | Not detected |
| 10 | 36 × 10$^6$ | Not detected | Not detected |
| 11 | 27 × 10$^6$ | Not detected | Not detected |

Note:
*below detection limit of 1 PFU per ml. The plaque assay images of repeat 1 samples are illustrated in FIG. 5.

REFERENCES FOR THE EXAMPLES

1. Adler, H., M. Messerle, M. Wagner, and U. H. Koszinowski. 2000. Cloning and mutagenesis of the murine gammaherpesvirus 68 genome as an infectious bacterial artificial chromosome. J Virol 74:6964-6974.
2. Allen, R. D., 3rd, M. N. DeZalia, and S. H. Speck. 2007. Identification of an Rta responsive promoter involved in driving gammaHV68 v-cyclin expression during virus replication. Virology 365:250-259.
3. Barton, E., P. Mandal, and S. H. Speck. 2010. Pathogenesis and host control of gammaherpesviruses: lessons from the mouse. Annu Rev Immunol 29:351-397.
4. Clambey, E. T., H. W. t. Virgin, and S. H. Speck. 2000. Disruption of the murine gammaherpesvirus 68 M1 open reading frame leads to enhanced reactivation from latency. J Virol 74:1973-1984.
5. Coleman, J. R., D. Papamichail, S. Skiena, B. Futcher, E. Wimmer, and S. Mueller. 2008. Virus attenuation by genome-scale changes in codon pair bias. Science 320: 1784-1787.
6. Mueller, S., J. R. Coleman, D. Papamichail, C. B. Ward, A. Nimnual, B. Futcher, S. Skiena, and E. Wimmer. 2010. Live attenuated influenza virus vaccines by computer-aided rational design. Nat Biotechnol 28:723-726.
7. Mueller, S., D. Papamichail, J. R. Coleman, S. Skiena, and E. Wimmer. 2006. Reduction of the rate of poliovirus protein synthesis through large-scale codon deoptimization causes attenuation of viral virulence by lowering specific infectivity. J Virol 80:9687-9696.
8. Pavlova, I., C. Y. Lin, and S. H. Speck. 2005. Murine gammaherpesvirus 68 Rta-dependent activation of the gene 57 promoter. Virology 333:169-179.
9. Pavlova, I. V., H. W. t. Virgin, and S. H. Speck. 2003. Disruption of gammaherpesvirus 68 gene 50 demonstrates that Rta is essential for virus replication. J Virol 77:5731-5739.
10. Quax, T. E., N. J. Claassens, D. Soll, and J. van der Oost. 2015. Codon Bias as a Means to Fine-Tune Gene Expression. Mol Cell 59:149-161.
11. Shen, S. H., C. B. Stauft, O. Gorbatsevych, Y. Song, C. B. Ward, A. Yurovsky, S. Mueller, B. Futcher, and E. Wimmer. 2015. Large-scale recoding of an arbovirus genome to rebalance its insect versus mammalian preference. Proc Natl Acad Sci USA 112:4749-4754.
12. Speck, S. H., and D. Ganem. 2012. Viral latency and its regulation: lessons from the gamma-herpesviruses. Cell Host Microbe 8:100-115.
13. Speck, S. H., and H. W. Virgin. 1999. Host and viral genetics of chronic infection: a mouse model of gammaherpesvirus pathogenesis. Curr Opin Microbiol 2:403-409.
14. Stahl, J. A., C. R. Paden, S. S. Chavan, V. MacLeod, R. D. Edmondson, S. H. Speck, and J. C. Forrest. 2012. Amplification of JNK signaling is necessary to complete the murine gammaherpesvirus 68 lytic replication cycle. J Virol 86:13253-13262.
15. van Dyk, L. F., H. W. t. Virgin, and S. H. Speck. 2000. The murine gammaherpesvirus 68 v-cyclin is a critical regulator of reactivation from latency. J Virol 74:7451-7461.
16. Virgin, H. W. t., P. Latreille, P. Wamsley, K. Hallsworth, K. E. Weck, A. J. Dal Canto, and S. H. Speck. 1997. Complete sequence and genomic analysis of murine gammaherpesvirus 68. J Virol 71:5894-5904.
17. Weck, K. E., M. L. Barkon, L. I. Yoo, S. H. Speck, and H. I. Virgin. 1996. Mature B cells are required for acute splenic infection, but not for establishment of latency, by murine gammaherpesvirus 68. J Virol 70:6775-6780.

What is claimed is:

1. A method of preventing or reducing viral reversion of a virus during culture, the method comprising:
   a) stably expressing a codon shuffled helper gene in a host cell, wherein the helper gene is codon modified to reduce expression of the helper gene in the host cell relative to the expression of an unmodified helper gene; and
   b) culturing the host cell under conditions conducive to the propagation of a replication incompetent virus, wherein the helper gene is deleted from the virus thereby rendering the virus replication incompetent.

2. The method of claim 1, wherein the virus is a DNA virus.

3. The method of claim 1, wherein the virus is a gene therapy vector.

4. The method of claim 2, wherein the virus is a gamma-herpesvirus.

5. The method of claim 1, wherein the replication incompetent virus comprises a deletion of replication and transcriptional activator (RTA) and the codon shuffled helper gene is ORF50.

6. The method of claim 1, wherein the helper gene comprises a sequence selected from the group consisting of SEQ ID NO:2, SEQ ID NO:3, SEQ ID NO:4, SEQ ID NO:5 and SEQ ID NO:6.

7. The method of claim 1, wherein viral reversion is prevented.

8. The method of claim 1, wherein the cell line is a fibroblast cell line.

9. The method of claim 1, wherein the codon shuffled helper gene is stably expressed via retroviral transduction.

10. A method of producing a viral stock composition, the method comprising:
    a) stably expressing a codon shuffled helper gene in a host cell, wherein the helper gene is codon modified to reduce expression of the helper gene in the host cell relative to the expression of an unmodified helper gene;
    b) culturing the host cell under conditions conducive to the propagation of a replication incompetent virus, wherein the helper gene is deleted from the virus thereby rendering the virus replication incompetent; and
    c) collecting the replicated virus.

11. The method of claim 10, wherein the virus is a DNA virus.

12. The method of claim 10, wherein the virus is a gene therapy vector expressing one or more genes of interest.

13. The method of claim 10, wherein the helper gene comprises a sequence selected from the group consisting of SEQ ID NO:2, SEQ ID NO:3, SEQ ID NO:4, SEQ ID NO:5 and SEQ ID NO:6.

14. The method of claim 10, wherein viral reversion is prevented.

15. The method of claim 12, further comprising step d) forming the composition comprising a gene therapy viral vector.

16. A composition comprising a gene therapy viral vector, wherein the viral vector was produced by the method of claim 15.

17. A vaccine composition, wherein the vaccine composition comprises virus produced by a method comprising:
    a) stably expressing a codon shuffled helper gene in a host cell, wherein the helper gene is codon modified to reduce expression of the helper gene in the host cell relative to the expression of an unmodified helper gene;
    b) culturing the host cell under conditions conducive to the propagation of a replication incompetent virus, wherein the viral genome comprises the deleted helper gene thereby rendering the virus replication incompetent;
    c) collecting the replicated virus; and
    d) forming the vaccine composition.

18. The composition of claim 17, wherein a pharmaceutically acceptable carrier or excipient is added to the vaccine composition.

19. The composition of claim 17, wherein the virus is a DNA virus.

20. The composition of claim 17, wherein the vaccine composition is formulated for oral administration, topical administration, parenteral administration or inhalation.

* * * * *